US012629267B2

(12) United States Patent
Gudjonsson et al.

(10) Patent No.: US 12,629,267 B2
(45) Date of Patent: May 19, 2026

(54) GROUND CONTACT SENSOR ARRAY FOR LOWER-LIMB PROSTHETIC AND ORTHOTIC DEVICES

(71) Applicant: ÖSSUR ICELAND EHF, Reykjavik (IS)

(72) Inventors: Sigurmundur Gudjonsson, Reykjavik (IS); Arni Einarsson, Reykjavík (IS); Hildur Inga Thorsteinsdottir, Reykjavik (IS); David Langlois, Saint-Jacques-de-Leeds (CA)

(73) Assignee: ÖSSUR ICELAND EHF, Reykjavik (IS)

( * ) Notice: Subject to any disclaimer, the term of this patent is extended or adjusted under 35 U.S.C. 154(b) by 906 days.

(21) Appl. No.: 17/638,493

(22) PCT Filed: Aug. 6, 2020

(86) PCT No.: PCT/US2020/045266
§ 371 (c)(1),
(2) Date: Feb. 25, 2022

(87) PCT Pub. No.: WO2021/040998
PCT Pub. Date: Mar. 4, 2021

(65) Prior Publication Data
US 2022/0401236 A1     Dec. 22, 2022

Related U.S. Application Data

(60) Provisional application No. 62/894,442, filed on Aug. 30, 2019.

(51) Int. Cl.
*A61F 2/76*      (2006.01)
*A61F 2/66*      (2006.01)
(Continued)

(52) U.S. Cl.
CPC .................. *A61F 2/76* (2013.01); *A61F 2/66* (2013.01); *A61F 2002/5083* (2013.01); *A61F 2002/704* (2013.01); *A61F 2002/762* (2013.01)

(58) Field of Classification Search
CPC ........ A61F 2002/7635; A61F 2002/762; A61F 2002/7612; G01L 1/12; G01L 1/122
See application file for complete search history.

(56) References Cited

U.S. PATENT DOCUMENTS 5,383,939 A     1/1995  James
5,406,845 A     4/1995  Berger et al.
(Continued)

FOREIGN PATENT DOCUMENTS

EP     3128958 A1     2/2017
GB     2302949 A  *  2/1997  ............. G01D 5/145
(Continued)

OTHER PUBLICATIONS

PCT Search Report and Written Opinion dated Oct. 19, 2020 regarding International Application No. PCT/US2020/045266, 15 pages.
(Continued)

*Primary Examiner* — Christie Bahena
(74) *Attorney, Agent, or Firm* — Knobbe, Martens, Olson & Bear, LLP

(57)                ABSTRACT

Systems, devices and methods for detecting ground contact with a lower-limb POD. A sensor array for the POD on a first or second body may include two or more sensors in an array that each detect a distance to a respective target on the other of the first or second body. The first and second bodies may move relative to each other thereby changing an offset distance or distances between the two bodies which is detected by the sensors. In some embodiments, the sensors may include Hall Effect sensors that detect distances to
(Continued)

respective magnets. Load data based on the detected distances may be generated for control of the POD, such as for stance phase control.

20 Claims, 18 Drawing Sheets

(51) Int. Cl.
    *A61F 2/50*           (2006.01)
    *A61F 2/70*           (2006.01)

(56)             References Cited

U.S. PATENT DOCUMENTS

| | | |
|---|---|---|
| 6,325,566 B1 | 12/2001 | Devine |
| 6,443,993 B1 | 9/2002 | Koniuk |
| 6,500,210 B1 | 12/2002 | Sabolich et al. |
| 6,610,101 B2 | 8/2003 | Herr et al. |
| 6,918,308 B2 | 7/2005 | Biedermann |
| 7,137,998 B2 | 11/2006 | Bédard et al. |
| 7,147,667 B2 | 12/2006 | Bédard et al. |
| 7,198,071 B2 | 4/2007 | Bisbee, III et al. |
| 7,410,471 B1 | 8/2008 | Campbell et al. |
| 7,475,606 B2 | 1/2009 | Selig et al. |
| 7,500,407 B2 | 3/2009 | Boiten |
| 7,597,017 B2 | 10/2009 | Bédard et al. |
| 7,655,050 B2 | 2/2010 | Palmer et al. |
| 7,736,394 B2 | 6/2010 | Bédard et al. |
| RE42,903 E | 11/2011 | Deffenbaugh et al. |
| 8,555,715 B2 | 10/2013 | Langlois et al. |
| 2002/0094919 A1 | 7/2002 | Rennex et al. |
| 2003/0029247 A1 | 2/2003 | Biedermann et al. |
| 2004/0086240 A1 | 5/2004 | Togami et al. |
| 2005/0107889 A1 | 5/2005 | Bédard et al. |
| 2006/0136072 A1 | 6/2006 | Bisbee et al. |
| 2006/0206215 A1 | 9/2006 | Clausen et al. |
| 2008/0046096 A1 | 2/2008 | Bédard et al. |
| 2008/0276725 A1 | 11/2008 | Pusch |
| 2009/0299480 A1 | 12/2009 | Gilbert et al. |
| 2010/0185124 A1 | 7/2010 | Bisbee, III et al. |
| 2011/0125290 A1 | 5/2011 | Langlois |
| 2012/0010729 A1* | 1/2012 | Langlois ................ A61F 2/70 |
| | | 600/587 |
| 2012/0083901 A1 | 4/2012 | Langlois et al. |
| 2018/0177618 A1 | 6/2018 | Langlois et al. |

FOREIGN PATENT DOCUMENTS

| | | |
|---|---|---|
| WO | WO 2012/006462 | 1/2012 |
| WO | WO 2021/040998 | 3/2021 |

OTHER PUBLICATIONS

International Search Report and Written Opinion in PCT Application No. PCT/US2011/043246, dated Nov. 21, 2011.

* cited by examiner

GROUND CONTACT SENSOR ARRAY FOR LOWER-LIMB PROSTHETIC AND ORTHOTIC DEVICES

CROSS-REFERENCE TO RELATED APPLICATIONS

The present application claims priority benefit to U.S. Provisional App. No. 62/894,442, entitled "GROUND CONTACT SENSOR ARRAY FOR LOWER-LIMB PROSTHETIC AND ORTHOTIC DEVICES," filed Aug. 30, 2019, which is hereby incorporated herein by reference in its entirety.

BACKGROUND

Field

The present disclosure is related to prosthetic or orthotic systems, in particular to systems and methods for a ground contact sensor array having one or more sensors to detect load applied to a lower-limb prosthetic or orthotic device for controlling the lower-limb prosthetic or orthotic.

Description of the Related Art

Various solutions exist for controlling lower-limb prosthetic and orthotic devices ("POD"). Typical solutions are limited by high cost of the components, the high level of integration required with the POD, and the reduction in performance due to various constraints associated with POD. These and other approaches inadequately deal with the asymmetry of acceleration spikes in transitioning from swing-to-stance versus stance-to-swing. This introduces complexity by relying heavily on advanced signal processing and interpretation. Therefore, improvements in controlling POD's based on ground contact detection are desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for detecting ground contact to control a lower-limb prosthetic or orthotic device ("POD").

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Features for systems, devices and methods for detecting ground contact with a lower-limb POD are described. A sensor array for the lower-limb POD may include two or more sensors, which may be non-contact displacement sensors, that can determine a change in distance between a moving part and a non-moving part of the lower-limb POD. A moving part or a non-moving part of the POD may support the sensors. Ground contact with the lower-limb POD may cause the offset distance between the moving part and the non-moving part to change. For instance, the distance from each of the sensors to respective target portions of the other body, such as respective portions of the moving body, respective magnets, or other respective targets, may be detected by the sensors. The sensors detect the change in this offset distance and generate data indicative of the load applied to the prosthetic device, which may be used to determine control signals for the lower-limb POD. A control system having a processor and memory may be used to receive and analyze the data, and generate the control signals accordingly. Various control approaches for lower-limb POD's based on the use of an array of non-contact sensors are described.

Various aspects and embodiments thereof described herein include, among other things, the use of a sensor array in a ground contact sensor with a selectively compliant mechanical structure. Further, the sensors are positioned in locations within the array configuration so as to maximize ground contact sensing system sensitivity to the loads observed during typical amputee ambulation. Further, a subset of the sensors may be used for sensor signals fusion and integration. Further, the system includes the capacity to integrate redundant sensing and allow recovering in case of sensor failure.

The various aspects and embodiments thereof described herein have various advantages. For example, limitations arising from ground contact structure overload are removed or reduced. Further, sensor sensitivity around the zero-load point up to the physiologically relevant load points is maximized or otherwise increased. Further, discrimination between torque loads and axial loads is possible, for instance by showing reduced mechanical response to torque loads. Further, requirements for precision in positioning the prosthetic device components in assembly and installation is reduced, for example by producing data showing the same sensitivity level for all load cases. Further, detection and identification of load progression direction is possible. Various other advantages are described in further detail herein.

In one aspect, a ground-contact sensor array for a lower limb prosthetic device is described that comprises a first body, a second body, and a plurality of sensors. The first body is configured to attach to a distal portion of a shank of the lower limb prosthetic device and has a first portion configured to remain stationary relative to the shank, with the first body comprising a second portion configured to compress in response to a ground contact load applied to the lower limb prosthetic device. The second body is moveably attached to and located distally of the first body and comprises a distal connector configured to attach to a prosthetic foot or ankle, with the second body configured to translate and/or rotate relative to the first body in response to the ground contact load applied to the lower limb prosthetic device to cause the second portion of the first body to compress. The plurality of sensors is coupled with a proximal portion of the first body and is configured to generate data related to a plurality of distances from the plurality of sensors to respective target portions of the second body in response to translation and/or rotation of the second body relative to the first body and/or in response to compression of the second portion of the first body, where the data is indicative of location of the second body relative to the first body, which is indicative of ground contact by the lower limb prosthetic device. In some embodiments, the plurality of sensors comprises Hall effect sensors and the respective target portions of the second body comprise magnets.

In another aspect, a ground-contact sensor array for a lower limb prosthetic device is described. The ground-contact sensor array comprises a first body, a second body, and a plurality of sensors. The first body is configured to attach to a shank of the lower limb prosthetic device. The second body is moveably attached to the first body and comprises a distal connector configured to attach to a prosthetic foot or ankle. The plurality of sensors is coupled with the first or second body and configured to generate data related to a plurality of distances between the first and second body.

Various embodiments of the various aspects describe herein may be implemented. The plurality of sensors may be coupled with the first body. The plurality of sensors may comprise non-contact distance sensors coupled with the first or second body and configured to generate data related to a plurality of distances to respective portions of the other of the first or second body. The ground-contact sensor array may further comprise a plurality of magnets coupled with the first or second body, where the plurality of sensors comprises a plurality of Hall effect sensors coupled with the other of the first or second body, and where each Hall effect sensor is configured to generate data related to a respective distance to a respective magnet.

The data related to a plurality of distances may comprise first data related to a plurality of first distances and second data related to a plurality of second distances, where the first or second data are generated in response to a non-inertial load applied to the lower limb prosthetic device, and where the first and second data are indicative of at least one of the plurality of first distances being different than at least one of the plurality of second distances. The plurality of sensors may be arranged in a transverse plane. The first body may be configured to not move relative to the shank and the second body may be configured to move relative to the first body.

The first body may comprise a selectively compliant structure. The selectively compliant structure may comprise a first pair of beams and a second pair of beams. The first pair of beams may be located on a medial side of the first body and extend in an anterior-posterior direction, with each beam of the first pair of beams spaced axially apart from each other. The second pair of beams may be located on a lateral side of the first body and extend in the anterior-posterior direction, with each beam of the second pair of beams spaced axially apart from each other. The ground-contact sensor array may further comprise a first bridge axially connecting the first pair of beams and a second bridge axially connecting the second pair of beams.

The data related to a plurality of distances between the first and second body may be generated in response to a ground-contact load applied to the first or second body during a stance phase of a gait cycle. The plurality of sensors may be configured to generate data related to a predetermined plurality of axial distances between the first and second body when no load is exerted on the second body.

The first body and second body may define a plurality of gaps therebetween. The plurality of gaps may be located between anterior and posterior ends of the first and second bodies. The gaps may change in size in response to relative movement between the first and second body. The first body may be attached to a raised surface of the second body located between the plurality of gaps.

In another aspect, a ground-contact sensor array for a lower limb prosthetic device is described. The ground-contact sensor array comprises a first body, a second body, and a plurality of sensors. The first body is configured to attach to a first portion of a lower limb prosthetic device that is located proximally of the first body. The second body is moveably attached to the first body and is configured to attach to a second portion of the lower limb prosthetic device that is located distally of the second body. The plurality of sensors is attached to the first or second body, and each sensor is configured to detect a respective distance between the sensor and a respective target of the other of the first or second body.

Various embodiments of the various aspects describe herein may be implemented. The plurality of sensors may be attached to the first body and each sensor may be configured to detect a respective distance between the sensor and the respective target of the second body. The respective target may comprise a respective portion of the other of the first or second body. The plurality of sensors may comprise a plurality of Hall effect sensors and the respective target may comprise a respective magnet. The plurality of sensors may be configured to generate a first set of data based at least on location of the first body relative to the second body, where the plurality of sensors are positioned in an array such that the first set of data represent distances at different locations to the other of the first or second body, and where the first set of data is representative of amount of load applied to different locations of the moving body and thereby provide a load pattern across the second body.

In another aspect, a lower limb prosthetic device is described comprising any of the ground-contact sensor arrays herein. The lower limb prosthetic device having the ground-contact sensor array may further comprise a prosthetic hip portion, a prosthetic thigh portion, a prosthetic shank portion, a prosthetic ankle portion, and/or a prosthetic foot portion.

In another aspect, a method of detecting ground-contact by a lower limb prosthetic device is described. The method comprises detecting first data related to a plurality of first distances between each sensor of a plurality of sensors and a moving body of the lower limb prosthetic device, detecting second data related to a plurality of second distances between each sensor of the plurality of sensors and the moving body of the lower limb prosthetic device, and determining that the lower limb prosthetic device has contacted ground based on the first and second data.

Various embodiments of the various aspects describe herein may be implemented. The method may further comprise detecting, using each of the plurality of sensors, a magnetic field generated by a plurality of magnets, determining a magnitude of the magnetic field detected by each of the plurality of sensors, and calculating the plurality of second distances based at least on the magnitude of the magnetic field.

In another aspect, a non-transitory computer readable medium is described. The non-transitory computer readable medium has stored thereon a set of instructions that when executed by a processor performs a method for determining a load pattern of a load applied to a lower limb prosthetic device. The method may comprise the above methods or any of the other methods described herein. In some embodiments, the method comprises measuring a first set of data using a plurality of sensors, the plurality of sensors coupled to a non-moving body of the prosthetic device and axially spaced apart at a predetermined distance from a moving body of the prosthetic device, the first set of data representative of relative motion between the non-moving body and the moving body of the prosthetic device, the moving body and the non-moving body coupled via a connector comprising a selectively compliant structure configured to resiliently flex under a load applied to the moving body. The method further comprises determining a second set of data using the first set of data, the second set of data comprising a plurality of electronic signals from the plurality of sensors, each of the plurality of electronic signals corresponding to an amount of load applied to different areas of the moving body of the prosthetic device, thereby providing a load pattern across the moving body of the prosthetic device. When a load is applied to the moving body, the selectively compliant structure resiliently flexes to change the distance between the plurality of sensors and the moving body. The change in the distance between the plurality of sensors and the plurality of actuators is representative of the relative motion between the non-moving body and the moving body.

In some embodiments, the method performed by the processor comprises calculating a plurality of first distances between each sensor of a plurality of sensors and a moving body of the lower limb prosthetic device, the plurality of sensors coupled to a non-moving body of the lower limb prosthetic device. The method further comprises calculating a plurality of second distances between each of the sensors of the plurality of sensors and the moving body of the lower limb prosthetic device, determining differences between each of the plurality of first distances and each of the plurality of second distances, and analyzing data related to the differences between each of the plurality of first distances and each of the plurality of second distances. The method further comprises determining that the lower limb prosthetic device has contacted ground in response to analyzing the data related to the between each of the plurality of first distances and each of the plurality of second distances.

In another aspect, a non-transitory computer readable medium is described having stored thereon a set of instructions that, when executed by a processor, performs the methods described herein for determining a load pattern of a load applied to a lower limb prosthetic device. The method performed may comprise measuring a first set of data using a plurality of sensors, with the plurality of sensors coupled to a non-moving body of the prosthetic device and axially spaced apart at a predetermined distance a moving body of the prosthetic device, the first set of data representative of relative motion between the non-moving body and the moving body of the prosthetic device, and the moving body and the non-moving body coupled via a connector comprising a selectively compliant structure configured to resiliently flex under a load applied to the moving body. The method may further comprise determining a second set of data using the first set of data, the second set of data comprising a plurality of electronic signals from the plurality of sensors, each of the plurality of electronic signals corresponding to an amount of load applied to different areas of the moving body of the prosthetic device, thereby providing a load pattern across the moving body of the prosthetic device. When a load is applied to the moving body, the connector may resiliently flex to change the distance between the plurality of sensors and the moving body, and the change in the distance between the plurality of sensors and the moving body may be representative of the relative motion between the non-moving body and the moving body.

According to another aspect of the present disclosure, a sensor assembly for a prosthetic device is described. The sensor assembly for a prosthetic device can include a connector comprising a selectively compliant structure disposed between a moving body and a non-movable body of the prosthetic device. The selectively compliant structure can move relative to the non-moving body. The selective compliant structure can include a first pair of blades disposed on a medial side of the connector and extending in an anterior-posterior direction. The first pair of planar blades can be spaced apart from each other. The selectively compliant structure can further include a second pair of blades disposed on a lateral side of the connector and extending in an anterior-posterior direction. The second pair of planar blades can be spaced apart from each other. The blades may flex to provide the relative movement between the bodies. The sensor assembly can further include a plurality of sensors coupled to the non-moving body. The plurality of sensors can be positioned in an array and sense the relative movement between the moving body and the non-moving body. The sensor assembly can further include a plurality of magnets coupled to the moving body. The plurality of magnets can be positioned at a predetermined axial distance from the plurality of sensors of the non-moving body when no load is exerted on the moving body. The first and the second pair of blades can resiliently flex to allow a relative movement between the connector and the non-moving body when the moving body is under a load. Each of the plurality of sensors can generate a first set of data based at least of the relative movement. The plurality of sensors can be positioned in an array such that the plurality of sensors represent different locations of the moving body. The first set of data can represent amount of load applied to different locations of the moving body, thereby indicating a load pattern across the moving body.

According to another aspect of the present disclosure, a method of determining a load pattern of a load applied to a lower limb prosthetic device is described. The method can include measuring a first set of data using a plurality of sensors. The plurality of sensors can be coupled to a non-moving body of the prosthetic device and axially spaced apart at a predetermined distance from a moving body of the prosthetic device. The moving body of the prosthetic device can comprise a plurality of magnets. The first set of data can represent relative motion between the non-moving body and the moving body of the prosthetic device, where the moving body and the non-moving body can be coupled via a connector that can resiliently flex under a load applied to the moving body. The method can further include determining a second set of data using the first set of data. The second set of data can include a plurality of electronic signals from the plurality of sensors, where magnitude of each of the plurality of electronic signals can correspond to an amount of load applied to different areas of the moving body of the prosthetic device. The second set of data can thereby provide a load pattern across the moving body of the prosthetic device. When a load is applied to the moving body, the connector can resiliently flex to change the distance between the plurality of sensors and the plurality of magnets. The change in the distance between the plurality of sensors and the plurality of magnets can represent the relative motion between the non-moving body and the moving body.

Figure 1:
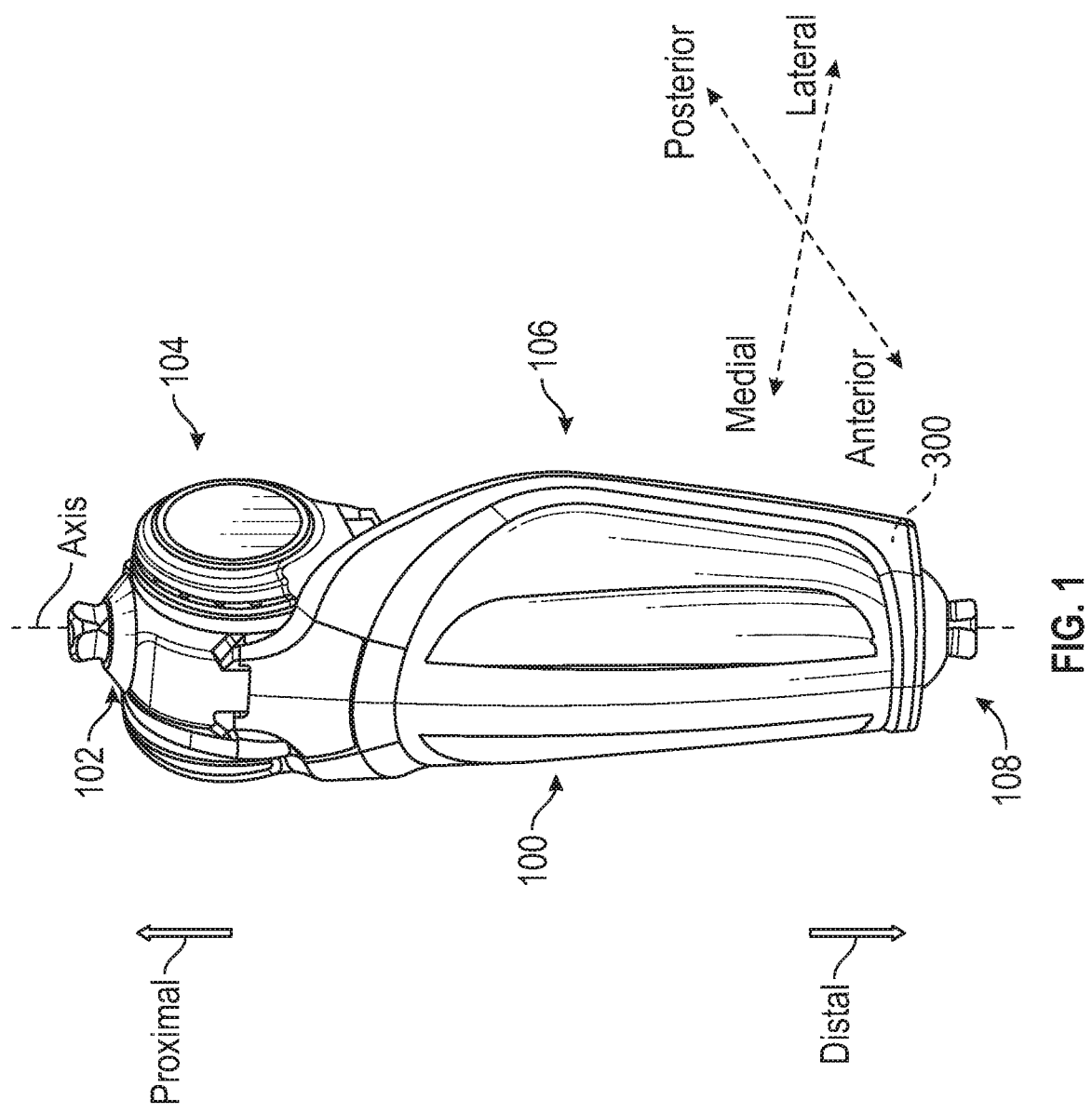
FIG. 1 is a perspective view of an embodiment of a lower-limb prosthetic device having an embodiment of a ground contact sensor array.

The foregoing and other features of the present development will become more fully apparent from the following description and appended claims, taken in conjunction with the accompanying drawings. Understanding that these drawings depict only several embodiments in accordance with the development and are not to be considered limiting of its scope, the development will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present development, as generally described herein, and illustrated in the drawings, can be arranged, substituted, combined, and designed in a wide variety of different configurations, all of which are explicitly contemplated and make part of this disclosure.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

Features for systems, devices and methods for detecting ground contact with a lower-limb POD are described. The lower-limb POD may include a first body and a second body. A sensor array for the lower-limb POD may include two or more sensors, such as non-contact displacement or other type sensors, coupled to the first or second body. The first and second bodies may be offset from each other and configured for relative movement between the bodies. The first body may move relative to the second body of the supporting structure, or vice versa, to change the offset distance between the sensors and the other of the first or second body. The first or second body may include one or more target portions sensed by the sensors. In some embodiments, the sensors are Hall Effect sensors and the target portions are magnets. Load data may be generated for control of the POD, such as for stance phase control. Control signals are generated based on the load data. In some embodiments, control signals are generated based on a magnetic field generated by the magnets and detected by the Hall Effect Sensors. Various control approaches for lower-limb POD's based on the use of an array of non-contact sensors are described.

The ground contact sensing techniques described herein allow for robust and high performance control of lower-limb POD's. The POD's may implement stance phase control with data from the ground contact sensing. Swing phase control may also be more robust when based on the ground contact sensing. Aspects described herein present a ground contact sensor array wherein a selectively compliant mechanical structure may be used. This may, for example, minimize the impacts of swing phase inertial perturbation on the sensor output, such that swing and stance phases are properly detected in a robust and timely manner.

The systems, devices and methods described herein provide advantages over other systems for detecting ground contact, such as those described, for example, in U.S. Pat. No. 8,555,715, titled "Ground Contact Sensing Systems and Methods for Lower-Limb Orthotic and Prosthetic Devices," and issued on Oct. 15, 2013, the entire contents of which are hereby incorporated by reference herein for all purposes and forms a part of this specification.

The systems, device and methods described herein may include ground contact sensing systems and methods that use a selectively compliant mechanical structure to allow discriminating inertial loads associated with phase from axial loads generated during stance phase. Using a plurality of, i.e. two or more, displacement sensors with the mechanically selective compliant structure allows for measuring occurrence of ground contact between the prosthetic limb and the ground, without having to deal with the dependencies of zero-load shift or overloading of the ground contact sensor assembly. Additionally, since the overload does not affect the sensor system itself, it is possible to control the maximum displacement of the flexible part of the mechanical structure, while maintaining the full sensor resolution around the zero-load point, effectively decoupling the two parameters.

In some embodiments, a load-cell may be used to measure the displacement of the flexible part of the mechanically selective compliant structure. The load-cell may be positioned substantially at the center of the assembly in the anterior-posterior direction. In some embodiments, the load cell may be positioned offset to one side in the coronal or frontal plane.

For a user's gait, vertical ground reaction force may not move in-line with the foot during stance phase, as foot rotation takes place during stance phase roll-over. Additionally, the amputee gait and foot alignment may seldom match what can be observed on non-amputated subjects. Furthermore, low proprioception and control over the residual limb may reduce the amputee capacity to apply sufficient loading to ensure that sufficient sensor output is generated in all use scenarios. The use of a plurality of non-contact sensors, as compared to a single non-contact sensor and other approaches, can address these and other issues. For example, use of a single non-contact sensor to average the ground contact reading with respect to the combined rotation and axial displacement of the assembly flexible part leads to decreased sensitivity on toe-load, and even further decreased sensitivity when a load cell with a single non-contact sensor is used and the load is applied on an opposite side from where the load cell is mounted. The array of non-contact sensors as further described herein overcome these and other drawbacks of existing approaches.

The features described herein have various advantages. Significant benefits and performance improvements are achieved when using a sensor array instead of, for example, a single sensor. For example, limitations arising from ground contact structure overload are removed or reduced. Further, sensor sensitivity around the zero-load point up to the physiologically relevant load points is maximized. Further, discrimination between torque loads and axial loads is possible, for instance by showing reduced sensitivity of torque loads. Further, dependency on the final details of the prosthetic device installation is reduced, for example by producing data showing the same sensitivity level for all load cases. Further, detection and identification of load progression direction is possible.

Other advantages include achieving repeatable measurements of loads applied to a lower-limb POD. The load applied to a lower-limb POD during a transition from swing phase to stance phase can be a small fraction of the total load registered when the user is standing still. In addition, in light of the shocks and overload possibility associated with the lower-limb POD, ensuring repeatable, accurate load measurements at a range of low and high loads is useful. The development described herein ensures both repeatable and accurate reading of small loads while still being capable of accurately registering high loads.

Additionally, the array improves capabilities related to "zero load" measurements and calibration-related issues. The development allows for stability of "zero load" measurements in view of perturbing influences, such as temperature changes, shocks, overload, electrical perturbations and exposure to humidity. The development allows for avoiding the complexities and impracticalities associated with taring to ensure zero-stability during use of the lower-limb POD. The development avoids the need for performing a calibration procedure or automating a zero-load calibration procedure, which can be cumbersome and prone to failure. This is useful since lower-limb POD's are submitted to various levels of load at almost all times during use.

Further, the array provides for reduced sensitivity to inertial loading through use of a selectively compliant mechanical structure, allowing at the same time sufficient compliance in the axial direction to properly measure occurrence of the foot strike event using a low-cost sensor.

Further, selective sensitivity may be achieved though the use of a selectively compliant mechanical structure with the sensor array. This may provide high stiffness to sagittal plane torque loading, e.g., foot generated inertial effects, while being highly compliant under axial loading.

Further, sensitivity for detecting specific types of loads applied to prosthetic devices can be increased. The foot-ground interaction can be properly characterized. The use of an array of sensors can minimize the impact or fully avoid any loss of sensitivity due to reduction of sensor and load line colinearity. These and other advantages, benefits, and uniquely desirable features will be apparent in the following detailed description.

Turning to the figures, FIG. 1 illustrates an embodiment of a prosthetic device 100 that includes an embodiment of a sensor assembly 300 therein. As further described herein, the sensor assembly 300 includes an array of sensors for detecting ground contact with the prosthetic device 100 and to control the device. The sensor assembly 300 is located at a distal end of the prosthetic device 100. This specific embodiment of the prosthetic device 100 is provided as merely one example. The sensor assembly 300 may be located at the proximal end of the prosthetic device 100, or in locations between the distal and proximal ends. Further, the features described herein may be applied to other embodiments, such as prosthetic feet, other lower limb prosthetics or orthotics, sensors for non-prosthetic or non-orthotic use, and other devices.

Anatomical reference directions for the anterior, posterior, lateral, and medial directions are indicated in FIG. 1 for the sake of description. The directions have their usual and ordinary meanings as known in the art. Anterior and posterior indicate directions in the sagittal or lateral plane toward the front and rear of the body, respectively. Medial and lateral indicate directions in the coronal or frontal plane generally toward the inner side and outer side of the body, respectively. As used herein, "anterior-posterior" indicates a direction along the sagittal plane, and "medial-lateral" indicates a direction along the coronal plane. The various terms may be used to indicate directions that are exactly along the corresponding planes, as well as directions that are angled relative to the planes but still at least partially in the direction.

The prosthetic device 100 illustrated in FIG. 1 implements a knee joint and may be connected to a user's residual limb, such as a thigh, through a socket (not shown) via the proximal connector 102 on its proximal end. The proximal connector 102 may be pyramidal in shape. The prosthetic device 100 is a lower-limb prosthetic device, shown as a shank. The proximal connector 102 may be coupled to an actuator 104, which can rotate with respect to a body 106. The actuator 104 may be motorized. Rotation of the actuator 104 may cause rotation of the proximal connector 102 with respect to the body 106, and vice versa. In some aspects, the body 106 may be on or form a shank portion of the prosthetic device 100. The body 106 may include electronic components, sensors, etc. (not shown) required for the prosthetic device 100 to operate, although in some aspects these components may be located elsewhere, such as on a peripheral device or within the components further described below. The prosthetic device 100 may be connected to a prosthetic or orthotic ankle or foot (not shown) via the distal connector 108 located on a distal portion of the prosthetic device 100. The prosthetic device 100 may be connected with or include a prosthetic hip, prosthetic thigh, prosthetic foot and/or prosthetic ankle.

Ground contact sensing systems described herein may be used to control an operation of a device such as the prosthetic device 100. The device 100 may incorporate various features and/or functions of other embodiments of lower-limb PODS's, and those various other POD's may be controlled with the system described herein, such as the lower-limb POD described in U.S. Patent Publication No. 2009/0299480, titled "Joint Actuation Mechanism for a Prosthetic and/or Orthotic Device having a Compliant Transmission," and published on Dec. 3, 2009, the entire content of which is hereby incorporated herein by reference for all purposes and forms a part of this specification.

Figure 2A:
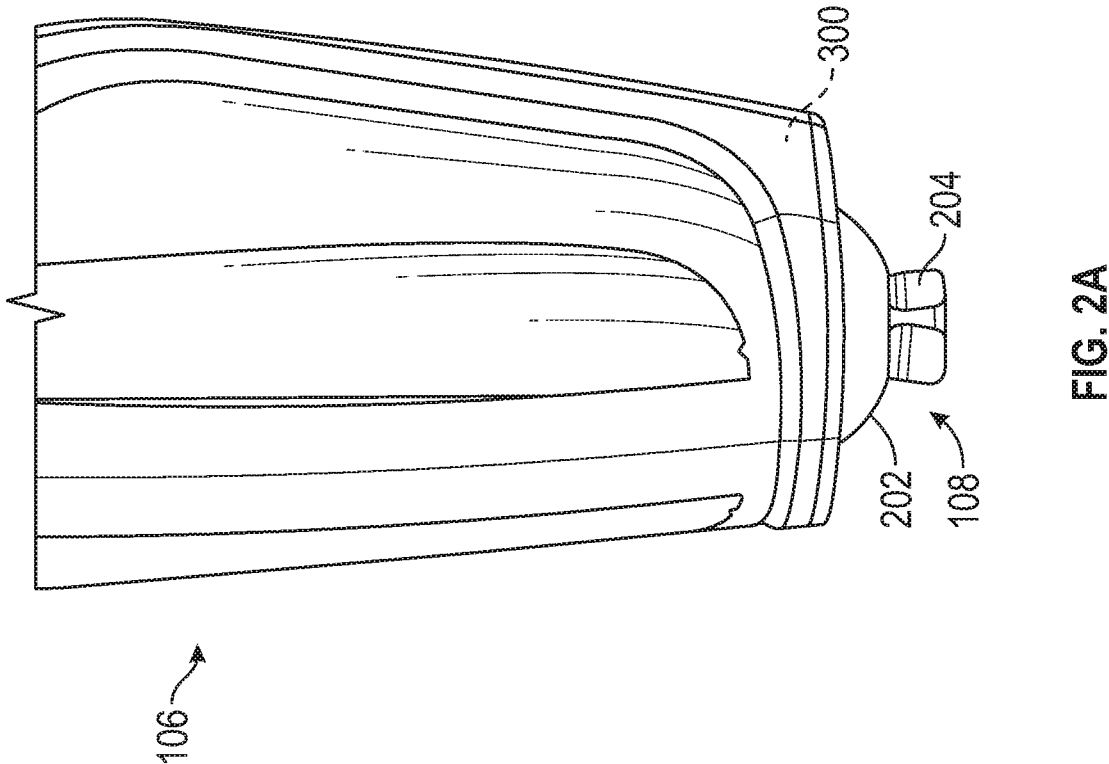
FIG. 2A is an enlarged view of a distal portion of the prosthetic device of FIG. 1 that includes the ground contact sensor array.

FIG. 2A is an enlarged view of the distal portion of the prosthetic device 100 having the sensor assembly 300 therein. The sensor assembly 300 is located partially within the device 100 and is thus labelled with a dashed line. The distal connector 108 may include a base 200 (see FIG. 2B), a mating surface 202, and/or a stud 204. The mating surface 202 may be dome-shaped and may extend away from a distal end of the body 106. In some embodiments, the mating surface 202 may be different shapes including, but not limited to, circular, rounded, square, hexagonal, other suitable shapes, or combinations thereof. The mating surface 202 may include an arcuate outer surface that may allow a smooth movement between the distal connector 108 and a prosthetic or orthotic foot or ankle coupled to the distal connector 108. The mating surface 202 may be a mating section that may be coupled to a corresponding mating section of a prosthetic or orthotic ankle or foot.

The stud 204 may be a protrusion extending distally from the mating surface 202. The stud 204 may be integrated with the mating surface 202 or separate from the mating surface 202. The stud 204 may be removably coupled to the mating surface 202 to allow users to use different types of studs or protrusions having different dimensions or shapes. In this regard, users may couple the prosthetic device 100 with different prosthetic devices having different types of connectors. The stud 204 may be square in shape or triangular, circular, hexagonal, or other shapes that allow removeable coupling between the distal connector 108 and a prosthetic or orthotic foot or ankle. The stud 204 may be dimensioned and/or shaped to minimize accidental detachment between the prosthetic device 100 and a prosthetic or orthotic ankle or foot.

Figure 2B:
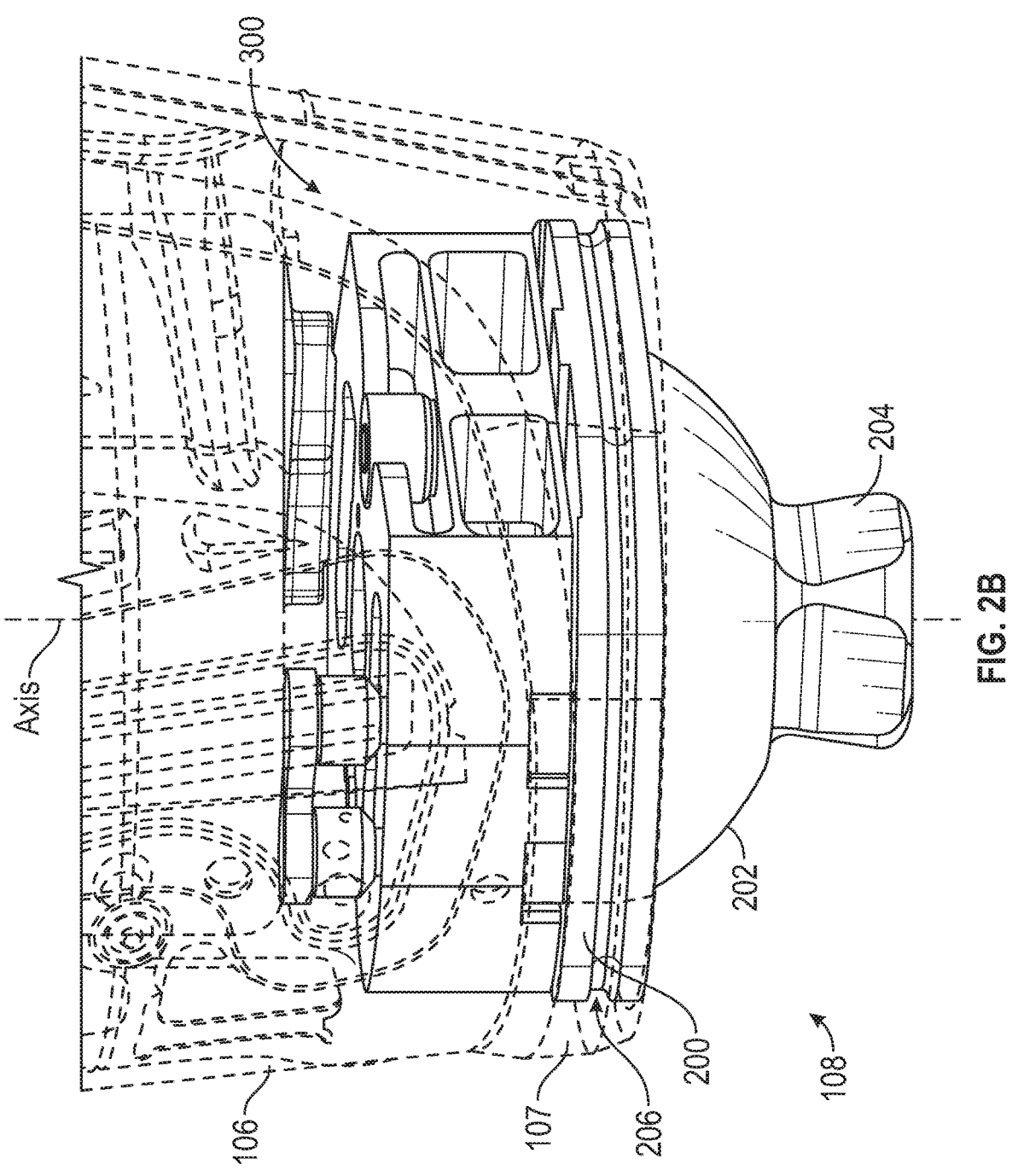
FIG. 2B is another enlarged view of the distal portion of the prosthetic device of FIG. 1 that includes the ground contact sensor array, with portions of the device shown transparently for clarity.

FIG. 2B shows the distal connector 108 with structural components of the body 106 shown transparently for clarity, for example to more clearly illustrate functional interactions between the structural components of the body 106, the sensor assembly 300, and the distal connector 108. The base 200 of the distal connector 108 may be mounted near a distal end of the body 106. In order to prevent ingress of solid parties or water, the connection between the base 200 of the distal connector 108 and the distal end of the body 106 may be sealed.

An annular recess 107 may be formed around an inner circumference of the distal end of the body 106. A sealing element may be inserted into the groove 107 of the distal end and between the body 106 and the base 200 to create a seal. In some embodiments, the base 200 may include an annular recess 206. The recess 206 may correspond to and couple with the recess 107 and sealing element located at the distal end of the body 106. The recess 206 may be formed around the entire circumference of the base 200. Alternatively, the recess 206 may be formed around a portion of the circumference of the base 200. One or more sealing elements may removably couple to the recess 206. A seal may be created between the distal end of the body 106 and the distal connector 108 by, for example, having a sealing element, such as an O-ring, removably coupled to the body 106 and the recess 206. The seal between the body 106 and the recess 206 of the distal connector 108 may prevent ingress of solid particles or water, which could impair proper function of the prosthetic device 100.

The distal connector 108 may be mounted near the distal end of the body 106 such that it is allowed to move axially in a proximal-distal direction, for example in a direction substantially parallel to the length of the body 106 of the prosthetic device 100. Additionally, the distal connector 108 may be constrained radially and/or in other directions such that it may not move in directions at angle to a longitudinal axis (as labelled in FIG. 2B) or other than the proximal-distal direction. In this regard, the distal connector 108 may only move, for example be pushed due to ground contact or other loads, proximally in a direction towards the proximal connector 102 of the prosthetic device 100, and/or move, for example be pulled due to gravity or inertial loads, distally in a direction away from the proximal connector 102.

The sensor assembly 300 may be coupled proximally of the distal connector 108 as shown. The sensor assembly 300 may be attached to a proximal end of the base 200, as further described herein. In some embodiments, the sensor assembly 300 may be located distally of the base 200, or in a more proximal location such as at a proximal end of the shank. The sensor assembly 300 may be located entirely or partially within the body 106, and thus the assembly 300 is labelled with dashed lines in FIGS. 1 and 2A. The body 106 and/or the connector 108 may cover the sensor assembly 300.

Figure 3A:
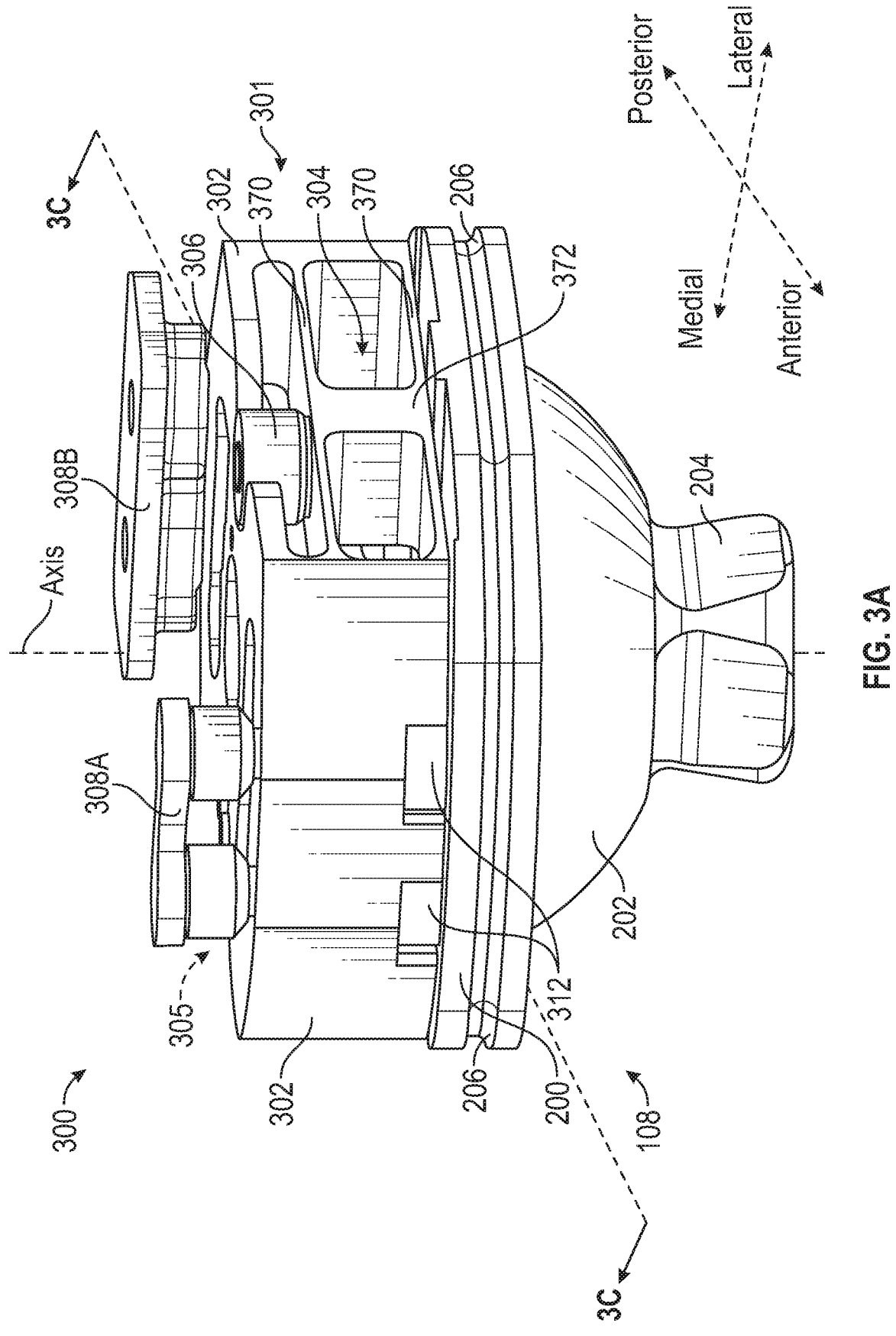
FIGS. 3A-3D are various views of the ground contact sensor array of FIGS. 1-2B.
Figure 3B:
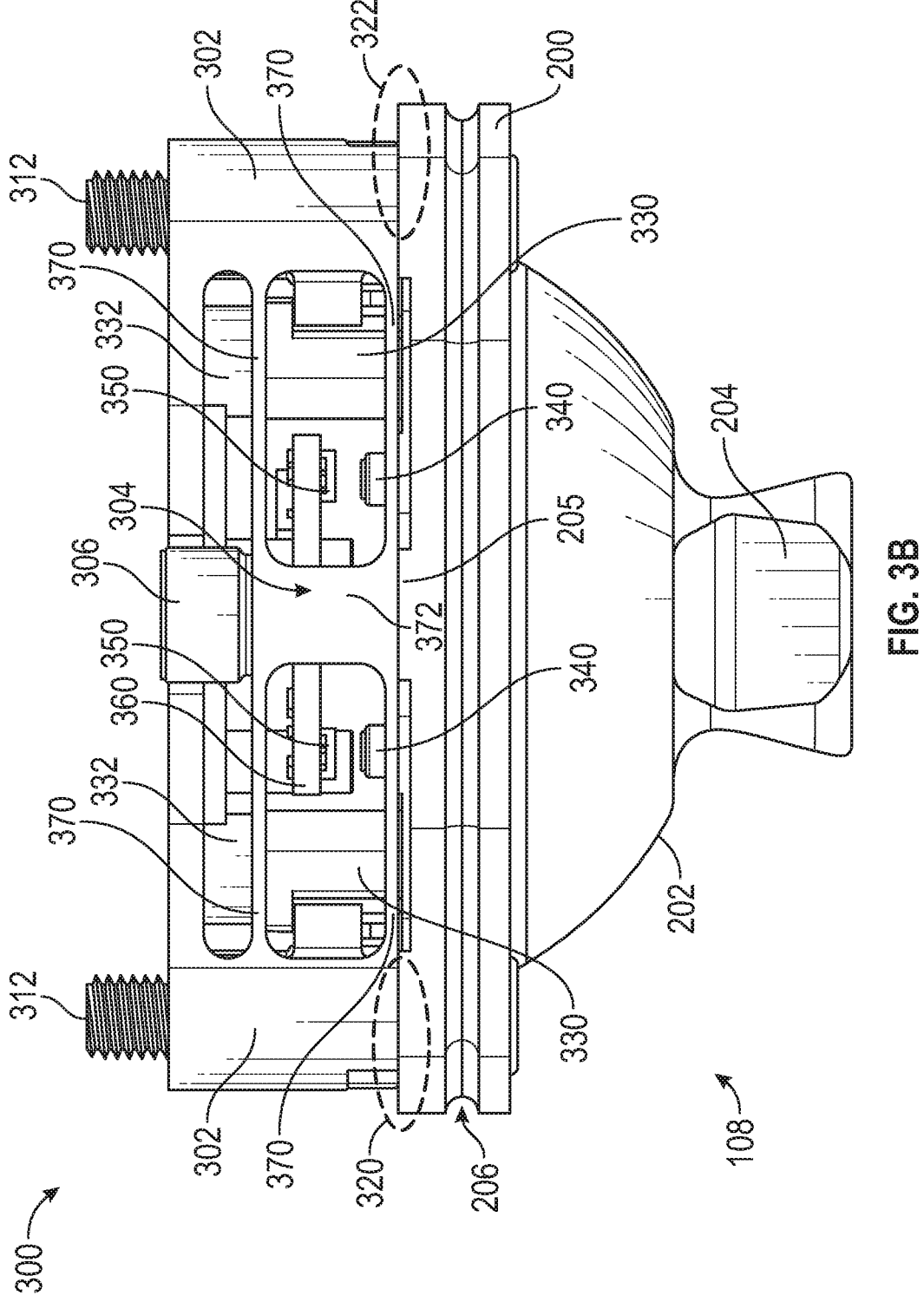
Figure 3C:
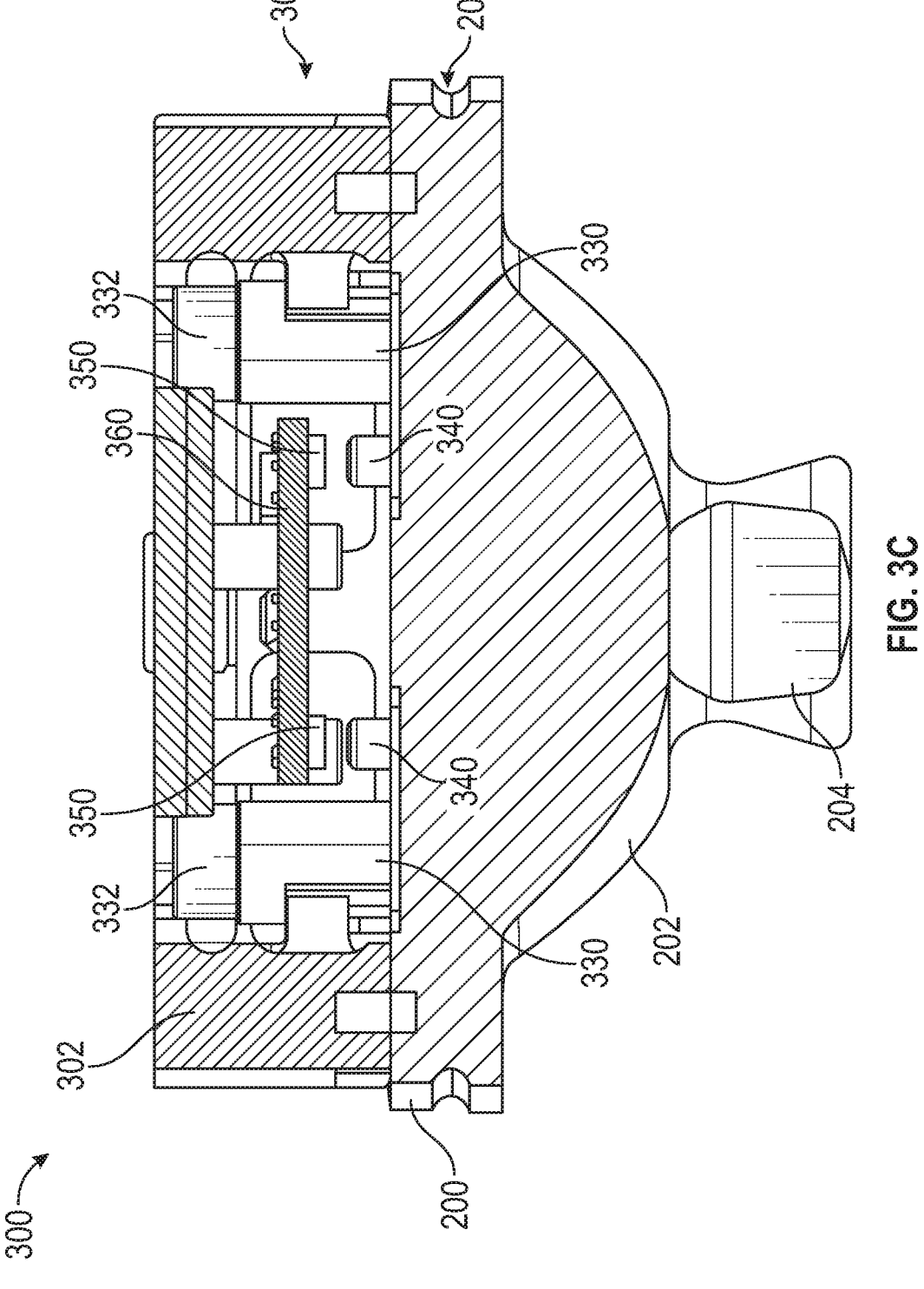
Figure 3D:
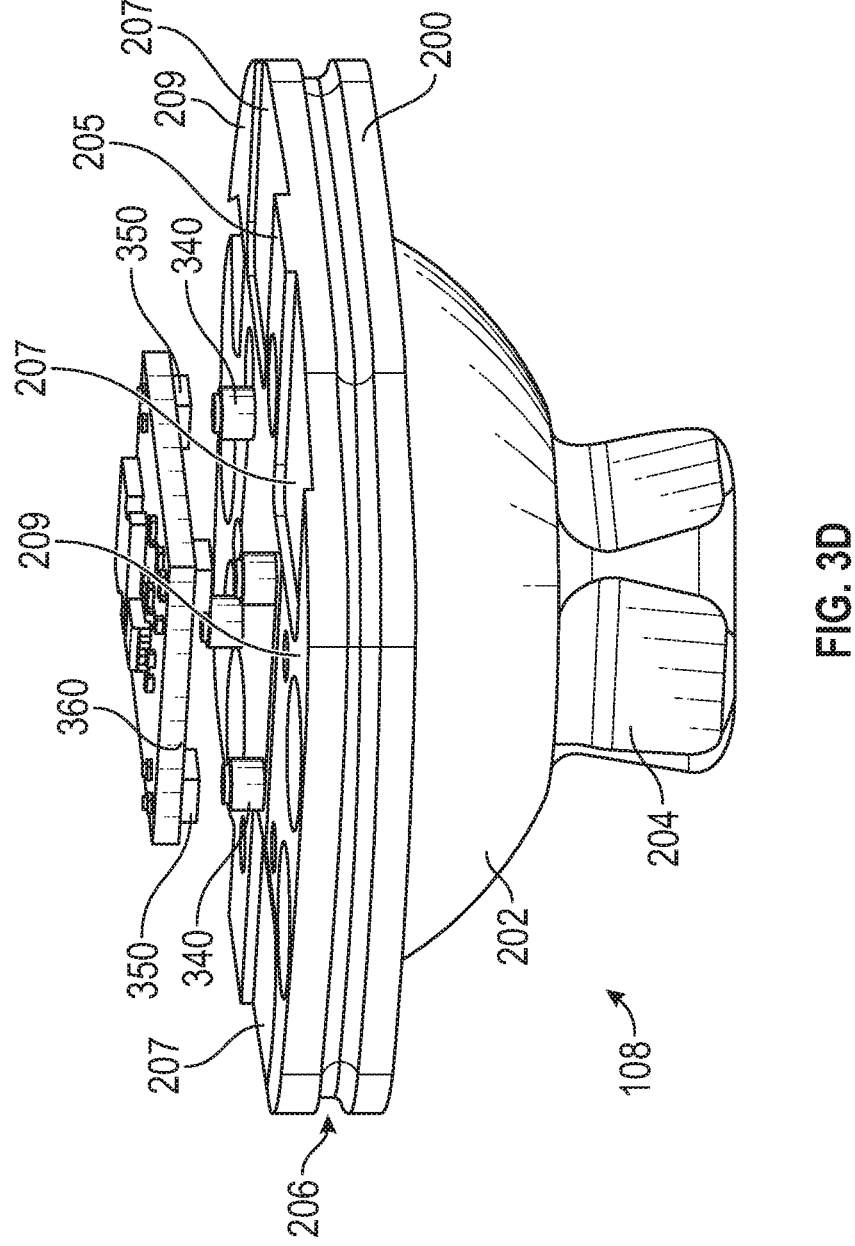

FIGS. 3A-3D are various views of the sensor assembly 300 attached to the distal connector 108. FIG. 3A is a perspective view of the sensor assembly 300. FIG. 3B is a side view of the sensor assembly 300. FIG. 3C is a cross-section view of the sensor assembly 300 as taken along the line 3C-3C indicated in FIG. 3A. FIG. 3D is a perspective view of the sensor assembly 300 with certain parts removed for clarity.

With reference to FIGS. 3A-3D, the sensor assembly 300 may be coupled to the distal connector 108. The sensor assembly 300 may be positioned adjacent to the base 200 opposite from the mating surface 202 and the stud 204, as shown in FIG. 3A. In some aspects, the sensor assembly 300 may be positioned within a recess formed about the distal end of the body 106 of the prosthetic device 100. The sensor assembly 300 or portions thereof may be fixedly coupled to the body 106 of the prosthetic device 100 such that some of the structure of the sensor assembly 300 remains stationary with respect to the body 106. The sensor assembly 300 may not translate or rotate relative to the body 106. A first portion of the sensor assembly 300 may not translate or rotate relative to the body 106, while another portion of the sensor assembly 300 may rotate and/or translate relative to the body 106, as further described herein.

The sensor assembly 300 includes a structural support 301. The structural support 301 may include a frame 302 and beam structures 304 and 305. The structural support 301 may include one or more first fasteners 306, one or more backing plates 308A, 308B, and/or one or more second fasteners 312. A portion of the structural support 301 is attached to a shank portion of the prosthetic device 100, such as the body 106, such that there is no relative movement between that portion of the structural support 301 and the shank portion, as further described. The frame 302 of the sensor assembly 300 may be affixed to the body 106 such that the frame 302, for example a portion of the frame 302 attached to the body 106, does not move with respect to the body 106 when a load is applied to the distal connector 108 in an axial direction. The frame 302 may include one or more apertures to accommodate for the fasteners 312 and fasteners 306. The one or more apertures may be threaded or not threaded. The fasteners 312 may fasten a first portion of the structural support 301 to the shank, and the fasteners 306 may fasten a second portion of the structural support 301 to the base 200, as further described.

The structural support 301 includes one or more beam structures. As shown, there is a first beam structure 304 located on a lateral side on the sensor assembly 300 and a second beam structure 305 located on a medial side of the sensor assembly 300 (for example for a left leg prosthetic). The second beam structure 305 is labelled in dashed line because it is not entirely visible as oriented in the figure. The beam structures 304, 305 may be symmetric, for example about the sagittal plane. The beam structures 304, 305 may include portions that extend in an anterior-posterior direction. Depending on the size of the beam structures 304, 305 and the size of the sensor assembly 300, one or more beam structures 304, 305 may be positioned on the medial side and the lateral side of the sensor assembly 300. The beam structures 304, 305 may be symmetric with respect to the sagittal plane and/or the coronal plane. There may be three, four, five or more beam structures.

As shown in FIG. 3A, there may be one beam structure 304 on the lateral side and one beam structure 305 on the medial side of the sensor assembly 300. In some embodiments, there may be two or more beam structures 304 on the lateral side and two or more beam structures 305 on the medial side of the sensor assembly 300. Additionally and/or alternatively, the sensor assembly 300 may have beam structures 304, 305 located on a posterior side and/or an anterior side, extending in a medial-lateral direction. As discussed above, there may be one beam structure on the posterior side and one beam structure on the anterior side. In some embodiments, there may be two or more beam structures on the posterior side and two or more beam structures on the anterior side. The number and/or locations of the beam structures 304, 305 of the sensor assembly 300 may change the degree of flexibility of the beam structures 304, 305 and thereby change responses of the beam structures 304, 305 under different load conditions, for example, different load conditions applied to the distal connector 108 during stance phase of gait.

Each of the beam structures 304, 305 may include two or more beams 370, such as plates. The beams 370 may be located in the anatomical transverse plane, which may be parallel to the base 200 of the distal connector 108. The beam structures 304, 305 may each include two beams 370 as shown in FIG. 3A. The beams 370 extend in an anterior-posterior direction. The beams 370 may extend in a plane such that the beams are stiffer in one direction and less stiff in a second direction that is different from the first direction. The beams 370 may be stiffer about the longitudinal axis (that is, axis parallel to the sagittal plane and extending in anterior-posterior direction) as compared to about axes perpendicular to the longitudinal axis. The beams 370 may extend in a plane parallel to the anatomical transverse or horizontal plane. The beams 370 may have a length in the anterior-posterior direction that is longer than a length in the medial-lateral direction. The beams 370 may have a thickness in the axial direction that is less than either or both of the length(s) in the anterior-posterior direction and the medial-lateral direction. In some embodiments, the beam structures 304, 305 may each include one, three, four, five, or more beams 370. The number of beams 370 may vary the degree of flexibility or compliance of the beam structure 304 against different load conditions.

Axially opposing beams 370 of the beam structures 304 may be connected via a bridge 372. The bridge 372 may extend axially (that is, in a proximal-distal direction) from about the middle portions of the anterior-posterior length of the opposing beams 370. The bridge 372 may have an anterior-posterior thickness that is different from an axial thickness of the beams 370. The anterior-posterior thickness of the bridge 372 may be greater than the axial thickness of the beams 370, as shown in FIGS. 3A and 3B. Alternatively, the anterior-posterior thickness of the bridge 372 may be equal to or less than the axial thickness of the beams 370. The pair of axially opposing beams 370 may be offset in a medial-lateral direction from the other pair of axially opposing beams 370 to define a space there between in which the sensor assembly 300 or portions thereof is located, as further described.

The bridge 372 may have a depth in the medial-lateral direction that extends coextensively with the medial-lateral depth of the beam structure 304 or portion thereof, for example the beams 370. Alternatively, the bridge 372 may have a depth that is greater than or less than the corresponding depth of the beam structure 304 or portion thereof. The depth of the bridges 372 may vary the flexibility and/or compliance of the beam structure 304 against different load conditions. The bridges 372 may be symmetrically positioned with respect to the sagittal plane and/or coronal plane.

The beams 370 of the beam structures 304 may be spaced axially apart from each other. The distance between the beams 370 may be sufficient to allow the beam structure 304 to be flexible and/or compliant against different load conditions, for example, during stance phase of a gait of the user. The distance between the beams 370 may be varied to vary stiffness of the beam structure 304 against torque loads. In some embodiments, the distance between the beams may not affect stiffness of the beam structure 304 against axial loads. As further described below, the compliance of the beam structure 304 of the sensor assembly 300 may allow accurate mapping of the load conditions applied on the prosthetic device 100, for instance due to ground contact. The beams 370 may be compliant such that they flex or compress axially in response to a load applied to the prosthetic device, such as a non-inertial ground contact load. The beams 370 may be configured to not compress or flex in response to an inertial load. One, some or all of the beams 370 may flex in response to a load.

As discussed above, the dimensions, numbers, and/or positions of the various features of the beam structures 304, 405, such as the beams 370, the bridges 372, etc., of the sensor assembly 300 may determine how the sensor assembly 300 and/or the beam structures 304, 305 respond to different load conditions. The beam structures 304, 305 may be positioned adjacent to the base 200 of the distal connector 108. In the example shown in FIG. 3A, the beam structures 304, 305 may be positioned up against the base 200 of the distal connector 108, on a side of the base 200 that is opposite from the mating surface 202 and the stud 204. The fasteners 306 may be used to fasten the beam structures 204 with the base 200.

Some portions of the beam structures 304, 305 may not be in direct contact with the base 200. In some embodiments, the portions at, toward and/or or near the center of the beam structures in the anterior-posterior direction 304, 305 may be in direct contact with the base 200 while the ends of the beam structures 304, 305 in the anterior-posterior direction are not in direct contact with the base 200. As shown in FIG. 3B, gaps 320, 322 may exist between distal portions of the anterior and posterior ends of the beam structures 304, 305 (that is, not the center portion of the beam structure 304) and a proximal side of the base 200. The size of the gaps 320 and/or 322 may be from about 0.05 mm to about 0.35 mm, from about 0.1 mm to about 0.3 mm, from about 0.15 mm to about 0.25 mm. The size of the gaps 320 and/or 322 may be 0.05 mm, 0.1 mm, 0.15 mm, 0.2 mm, 0.25 mm, 0.3 mm, 0.35 mm, 0.4 mm, 0.45 mm, 0.50 mm, or more. The size of the gaps 320 and/or 322 may be between ranges of any two of the various aforementioned values. The gaps 320 and 322 may be the same or different in size. The gaps 320, 322 may be measured axially between opposing portions of the support structure 301 and the base 200.

The gaps 320, 322 may be located such that the frame 302 and/or other portions of the support structure 301 may be able to move relative to the base 200 and/or mating surface 202. The support structure 301, for example the frame 302 that supports the PCB 360 and sensors 350 thereon, may thus not move relative to the shank or other proximal portion of the prosthetic device 100. The base 200 may move relative to the support structure 301 that supports sensors 350, as further described. Such movement may be due to ground contact and other loads during stance phase.

The frame 302 may be able to move by flexing and/or rotating about the anterior-posterior direction and/or about the medial-lateral direction. The beams 370 may flex, as described. The frame 302 or portions thereof may flex about a first raised portion 205 of the distal surface of the base 200. The first raised portion 205 may extend along the surface of the base 200 and partially define one or more recesses 207. The first raised portion 205 may extend in a medial-lateral direction. There may be a second raised portion 209 located on anterior and posterior sides of the first raised portion 205. The second raised portion 209 defines surfaces that are located distally of, or lower than, the surface of the first raised portion 205. The second raised surfaces partially define the recesses 207. The higher first raised portion 205 allows for a level distal surface of the frame 302 to result in the gaps 320, 322 when assembled with the base 200. Other configurations may be implemented to result in the gaps 320, 322, such as a non-level distal surface of the frame 302, the use of spacers or shims on either a proximal surface of the base 200 and/or a distal surface of the frame 302, etc.

A top surface of the base 200, such as the raised portion 205, may define a first abutment surface and a bottom surface of the frame 302 facing the base 200 may define a second abutment surface. As discussed above, the first abutment surface of the base 200 can include one or more recesses 207 and raised portion 205. Alternatively, the first abutment surface of the base 200 can be flat. The second abutment surface of the frame 302 can be level. The beam structures 304, 305 can define at least a portion of the second abutment surface of the frame 302. The non-moving body and the moving body of the device 100 can be coupled such that the first abutment surface of the base 200 and the second abutment surface of the frame 302 can be adjacent to each other.

A first or second body of the sensor assembly 300 may move relative to the other of the first or second body. As shown, the base 200 may translate and/or rotate relative to the structural support 301. The base 200 may rotate about the raised surface 205. The base 200 may translate axially. Such movements may change the size of the gaps 320, 322. The gaps 320, 322 may change to zero distance such that the moving body has reached a maximum relative axial movement relative to the non-moving body and the two bodies abut each other in the locations of the gaps 320, 322. The various movements of the moving body relative to the non-moving body cause changes in the distances between the two bodies that the sensors 350 then detect to determine ground contact, as described herein.

In some embodiments, there may not be the gaps 320, 322. In some embodiments, the gaps 320, 322 may be in different locations. The structures may have these gaps in a resting state where no external loads other than those due to the weight of the various structures are applied, i.e. without ground contact.

In some embodiments, the base 200 is suspended from the structural support 301, such as from the beam structures 304, 305, of the sensor assembly 300. Since the beam structures 304, 305 may be compliant and thus flex when load is applied in the distal-proximal direction, additional structures may be provided to limit the effects of loads causing a distal pull on the base 200. The backing plates 330 may attach to the shank of the prosthetic device 100 and to the base 200. The backing plates 330 may be connected to the shank and/or base 200 via fasteners 332. Connection of the base 200 with the shank may prevent or limit the sensor assembly 300 and the base 200 of the distal connector 108 from moving in a distal direction. The backing plates 330 may thus limit displacement of the base 200 under distal pull forces. The backing plates 330 may be rigidly connected to the base 200 and/or the shank via the fasteners 332. The backing plates 330 may extend axially with an opening therethrough. The backing plates 330 may be separate from the base or integral therewith. The backing plates 330 may extend through the support structure 301. The backing plates 330 may be located in between the two beam structures 304, 305. The backing plates 330 may be located on a medial side of the beam structure 304, on a lateral side of the beam structure 305, on a posterior side of the anterior portion of the frame 302, and/or on an anterior side of the posterior portion of the frame 302.

The backing plates 308A, 308B may connect the support structure 301 to the shank, as mentioned. The backing plates 308A, 308B and the corresponding fasteners 312 may be provided in the anterior and/or posterior areas of the sensor assembly 300. Most of the load applied to the prosthetic device 100 may be applied to anterior and posterior section of the sensor assembly 300. The backing plates 308A, 308B may therefore be located in the anterior and posterior sections, for example to limit movement of a moving part (e.g., the base 200) of the prosthetic device 100. The backing plates 308A, 308B may be fixed to the shank, such as the body 106, via the fasteners 312. Additionally and/or alternatively, the backing plates 308A, 308B and the corresponding fasteners 312 may be provided in the medial and/or lateral areas of the sensor assembly 300. The backing plates 308A, 308B may be symmetrically positioned with respect to the sagittal plane and/or the frontal plane.

Various portions of the structural support 301 may move and other portions may not move in response to an applied load. A portion of the support 301 attached to the body 106 may not move. A portion of the support 301 attached to the distal connector 108 may move, for example flex. Further, the distal connector 108 or portions thereof may move relative to the support 301. As further described herein, the base 200 or other portions may translate, rotate, or translate and rotate relative to the support 301. Such movement may be detected by sensors to determine ground contact, as further described.

The sensor assembly 300 may include a plurality of sensors 350. The sensors 350 may be non-contact or other type sensors that detect a distance from the sensor to another object without contacting that other object. The other object may be a target portion of an opposing structure, a magnet, or other object. The sensors 350 may be attached to the moving or non-moving portion of the structure. The sensors 350 may be attached to the non-moving portion, such as an upper part of the support 301 that does not move relative to the shank or other portion of the prosthetic body, and may detect a plurality of distances between each sensor and an opposing respective target, such as a respective portion or region of the moving body portion. In some embodiments, the sensors 350 are Hall effect sensors that detect a distance to an opposing respective magnet. In some embodiments, the sensors 350 may be contact sensors.

The sensors 350 may be coupled to a printed circuit board (PCB) 360. The PCB 360 may be rigidly coupled to a portion of the frame 302 such that the PCB 360 does not move with respect to the frame 302 under different load conditions. The frame 302 in turn is rigidly connected to the shank or other portion of the prosthetic device 100 that is proximal of the base 200. Thus the sensors 350 do not move relative to the shank or other portion. When a load is applied to the prosthetic device 100, the beam structures (for example, beam structures 304, 305) of the sensor assembly 300 can flex to change the distance between the base 200 and the frame 302. The sensors 350, in turn, can detect changes in the distance between the base 200 and the frame 302. The sensors 350 may be separate physical sensors, or separate areas of sensitivity of one larger sensor.

The sensors 350 may be any type of proximity or distance sensor. For example, the sensors 350 may be non-contact sensors, contact sensors, inductive sensors, capacitance sensors, photoelectric sensors, through-beam sensors, retro-reflective sensors, diffuse sensors, ultrasonic sensors, other suitable sensors, or a combination thereof. In some embodiments, other non-contact displacement sensors may be used. For example, the various sensors may be inductive displacement sensors, optical displacement sensors, time-of-flight sensors (laser, IR, ultrasound, etc.), other suitable sensors, or combinations thereof.

Additionally, the sensor assembly 300 may include one or more magnets 340 coupled to the base 200. The magnets 340 are one example of targets that the sensors 350 may detect. Other targets may be used, such as respective regions or portions of the opposing structure, such as a top surface of the base 200, that moves relative to the structure on which the sensors 350 are mounted. Thus any description of the magnets 340 herein may be applicable to other types of targets for the sensors 350.

The magnets 340 may be oriented to face in the proximal direction, for example towards the proximal connector 102 of the prosthetic device 100. The magnets 340 are capable of generating a magnetic field in surrounding areas. As shown, the sensors 350 are magnetic sensors that detect the magnetic field generated by a corresponding magnet 340. The sensors 350 may generate an output indicative of the magnitude of the magnetic field of a respective magnet 340 that the sensor 350 is detecting. The sensors 350 may be Hall effect sensors. The sensors 350 may be transducers that vary an output voltage in response to the magnetic field from the actuators 340, which output voltage may be directly proportional to the strength of the magnetic field through the sensor 350.

As the base 200 with the magnets 340 moves relative to the frame 302, the magnets 340 and sensors 350 correspondingly move relative to each other. The magnets 340 and the sensors 350 may be at a first offset distance from each other when no load is applied to the prosthetic device 100. When a non-inertial load is applied to the prosthetic device 100, the offset distance between the magnets 340 and the sensors 350 may change to a second offset distance. The difference between the first offset distance and the second offset distance can correspond to the amount of load applied to the prosthetic device 100. Additionally, the magnets 340 and the sensors 350 may be arranged in an array (see FIGS. 4, 5, and 5B). The sensors 350 may be arranged in an array. The sensors 350 may be arranged in the transverse plane, sometimes referred to as the horizontal plane. As used herein, "transverse plane" has its usual and customary meaning, and includes without limitation a plane perpendicular to the coronal and sagittal planes and which may divide the body into relative upper and lower portions. The arrangement of the sensors 350 and their target sensing portion, such as the magnets 340, may advantageously allow the prosthetic device 100 to collect data representative of load applied to the prosthetic device 100 during a gait cycle and characteristics of that load, as further described below. The magnets 340 may be separate from each other as shown. In some embodiments, a single larger sensor with separate areas of sensitivity may be used and still fall under the scope of a "plurality" of sensors.

In some embodiments, at least a portion of the base 200 includes a magnetic element that can generate a magnetic field around the sensor assembly 300. For example, a top surface of the base 200 facing the sensors 350 can be magnetic. In another example, at least a portion of the beam structures 304, 305 or the mating surface 202 can be magnetic such that the sensors 350 can detect changes in the magnitude of a magnetic field generated by the beam structures 304, 305 or the mating surface 202 under different load conditions.

The sensors 350 may be positioned such that they are an initial offset distance apart from the base 200 when no load is applied to the prosthetic leg by the ground. The initial distance between the base 200 and the sensors 350 may represent a zero-load condition. When a load due to ground contact is applied to the prosthetic device 100, the load may cause relative movement between the base 200 and the frame 302 of the support structure 301 of the sensor assembly 300, thereby changing the offset distance between the base 200 and the sensors 350. As discussed above, the change in the distance between the base 200 and the sensors 350 may directly correspond to the amount of load applied to the prosthetic device 100. The change in distance will produce a change in voltage generated by the non-contact sensors, which can be analyzed to determine ground contact, as further described.

Under different load conditions, the beam structures 304 and/or 305 of the sensor assembly 300 may be compressed at least in an axial direction to reduce the distance between the base 200 and the sensors 350. In the example in which the base 200 includes the magnets 340, the magnets 340 may move proximally. In this regard, the change in proximity of the magnets 340 and the sensors 350 may change the strength of the magnetic field surrounding the sensors 350. For example, reduced distance between the magnets 340 and sensors 350 may increase the magnitude of the magnetic field detected by the sensors 350. The increase in the magnitude of the magnetic field detected by the sensors 350 may represent the change in the distance between the magnets 340 and the sensors 350, which may represent the change in the distance between the sensor assembly 300 and the base 200, which may be analyzed to determine the presence and/or characteristics of ground contact by the prosthetic device. The sensors 350 may generate signals corresponding to the change of the magnetic field. In some aspects, the sensors 350 may detect changes in the amount of current or voltage generated by the sensors 350 due to the magnetic field generated by the magnets 340. The changes in distance detected by the sensors 350 may be caused by axial translation movement of the base 200 relative to the structure 301, by transverse translational movement of the base 200 relative to the structure 301, and/or by rotational movement of the base 200 relative to the structure 301 about any three orthogonal axes.

As discussed above, the beam structures 304, 305 of the sensor assembly 300 may allow selective compliance under different load conditions. While the beam structure 304 may be compliant to an axial load (distal-proximal direction), it may be relatively more rigid or less compliant to loads in the anterior-posterior and/or medial-lateral directions. The degree of compliance of the beam structure 304 may be varied by changing various dimensions of the beam structure 304.

The selective compliance of the support structure 301 and the array of the sensors 350 allow for more accurate detection of loads due to ground contact. The separation distance between axially opposing beams 370 provides rigidity in response to sagittal plane torque loads. Thus the sensors 350 are less likely to move or to move as much due to such loads, which may be applied due to influences other than ground contact, such as inertial loads during swing phase. Therefore axial loads during stance phase due to ground contact are better isolated and detected. This results in less complex signal processing as compared to other approaches, as discussed herein.

The configuration of the support structure 301 and base 200 allow for relative movement between the two structures. Since the support structure 301 may be rigidly attached to the shank or other portion of the prosthetic device 100, movement of the base 200 as detected by the sensors 350 corresponds to relative movement between the base 200 and supports structure 301. Thus the resulting voltage changes detected by the sensors 350 is indicative of the relative movement of the respective structures. The layout of multiple sensors 350 in an array with such structural configurations can result in robust and reliable output data.

Figure 4:
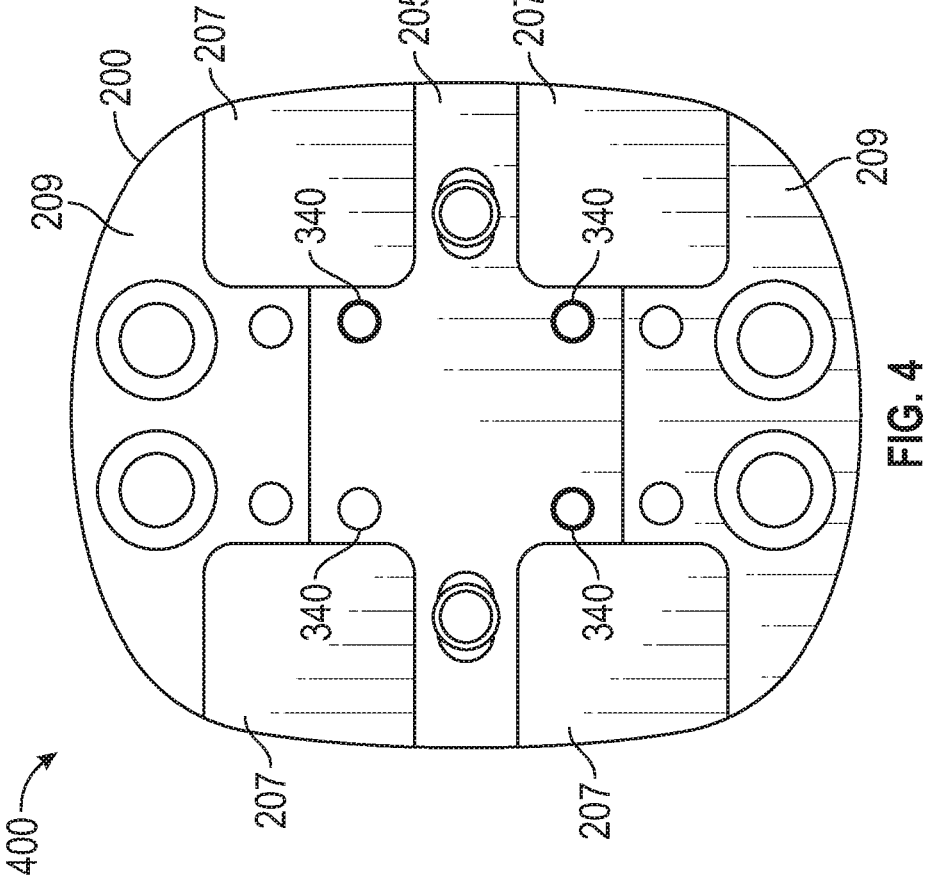
FIG. 4 is a top view of an embodiment of a moveable body in an example sensor assembly that can be used in the ground contact sensor array of FIGS. 1-3D.

FIG. 4 illustrates an example array 400 of the magnets 340. As discussed above, the magnets 340 may be coupled to the base 200 of the distal connector 208. There may be four magnets 340 coupled to the base 200 as shown in FIG. 4. In some aspects, there may be less than four magnets 340 coupled to be base 200. In other aspects, there may be more than four magnets 340 coupled to the base 200. The magnets 340 may be arranged in symmetry with respect to the sagittal plane and/or coronal plane. The magnets 340 may be in symmetry with respect to any other planes. In some aspects the magnets 340 may be arranged in point symmetry with respect to a predetermined location of the sensor assembly 300 or the base 200. The magnets 340 may be positioned equidistant from each other. The magnets 340 may be positioned in a square array (as shown in FIG. 4), a rectangular array, a circular array, an oval array, a hexagonal array, and the like.

In some embodiments, the magnets 340 can be integrated with the base 200. In other embodiments, as discussed above, the base 200 can be made out of magnetic material such that at least a portion of the base 200 is magnetic and generates a magnetic field around the sensor assembly 300.

Figure 5A:
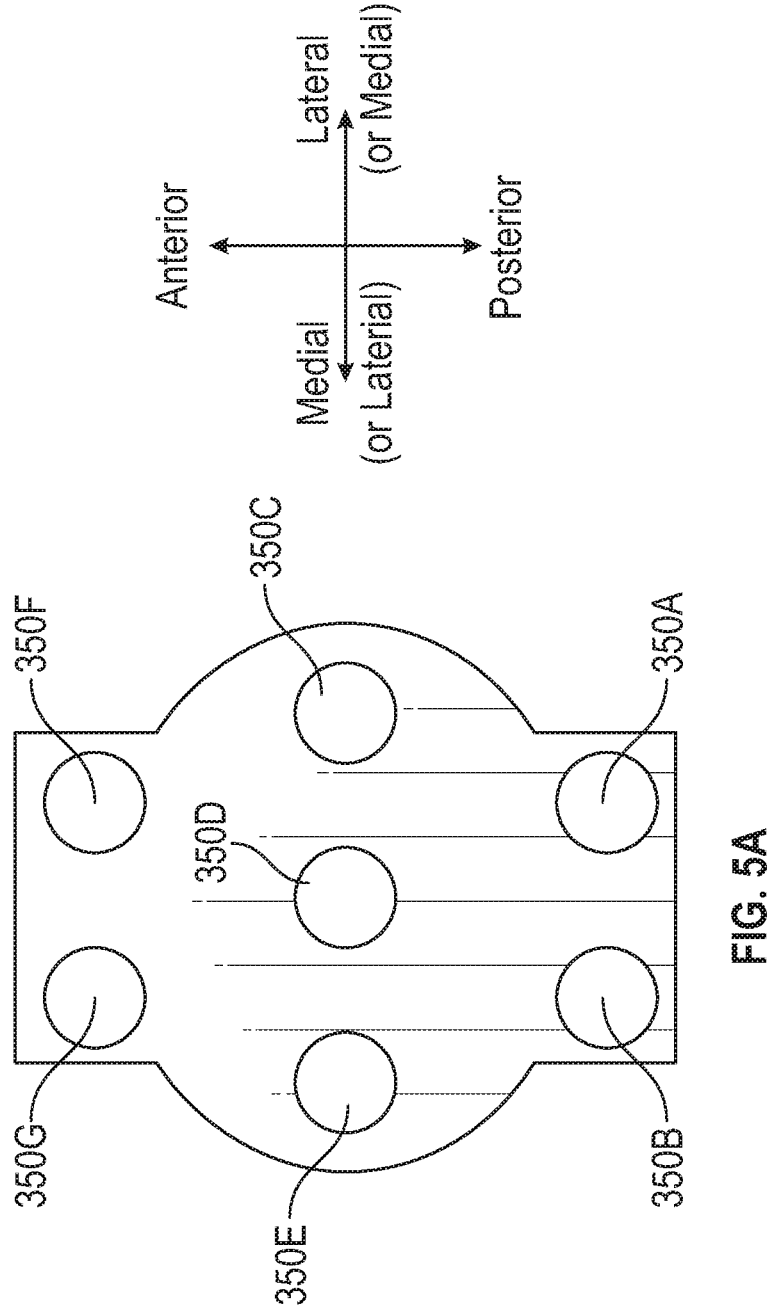
FIG. 5A is a bottom view of an embodiment of an array of sensors of an example sensor assembly that can be used with the ground contact sensor array of FIGS. 1-4.

FIG. 5A illustrates an example array 500 of the sensors 350 coupled to the PCB 400. The sensors 350F and 350G may be positioned in the anterior portion of the PCB while the sensors 350A and 350B may be positioned in the posterior portion of the PCB. The sensors 350C, 350D, and 350E may be positioned between the rest of the sensors (that is, sensors 350A, 350B, 350F, and 350G).

The array 500 of the sensors 350 on the PCB 400 may be symmetric in one or more ways. For example, the sensors 350C, 350D, and 350E may define an axis of symmetry for the sensors 350F and 350G the sensors 350A and 350B. In this regard, the distance between the axis of symmetry defined by the sensors 350C, 350D, and 350E and the sensors 350F and 350G may be the same as the distance between the axis of symmetry and the sensors 350A and 350B. In some aspects, the sensors 350C, 350D, and 350E may define the coronal plane that bisects the sensor assembly 300 into an anterior region and a posterior region.

The sensors may be in symmetry with respect to the sagittal plane that bisects the sensor assembly 300 into a medial side and a lateral side. In the example illustrated in FIG. 5A, the sagittal plane may extend between the front side and the rear side through the sensor 350D. In this regard, the sensor 350G and the sensor 350F may be in line symmetry with respect to the sagittal plane. Likewise, the sensors 350C and 350E, and the sensors 350A and 350B may be in line symmetry with respect to the sagittal plane. In some aspects, the sensors 350 may be in symmetry with respect to any other plane.

A point symmetry may exist between the sensors 350A-350G of the sensor array 500 illustrated in FIG. 5A. The sensor 350A may be in point symmetry with the sensor 350G with respect to the sensor 350D. Similarly, the sensor 350B may be in point symmetry with the sensor 350F with respect to the sensor 350D. The sensor 350C may be in point symmetry with the sensor 350E with respect to the sensor 350D.

The symmetry between the sensors 350 may prevent reduction of sensor sensitivity during gait. Typical ground-foot interaction during level walking gait is characterized by an initial contact taking place on the lateral side of the heel and progressing towards the big toe during the stance phase roll-over. Center of pressure line then crosses over the foot during the stance phase roll-over. By having an array of sensors 350, the sensors 350 may remain colinear with the force application points throughout the roll-over, thereby preventing reduction of sensor sensitivity. In other words, the sensors 350 together will not experience what is perceived by the control system as a reduction of load during the stance phase roll-over.

For right leg/foot amputees, the sensors 350B, 350E, and 350G may represent sensors 350 located on a medial side, while the sensors 350A, 350C, and 350F may represent sensors 350 located on a lateral side. On the other hand, for left leg/foot amputees, the sensors 350B, 350E, and 350G may represent sensors 350 located on a lateral side, while the sensors 350A, 350C, and 350F may represent sensors 350 located on a medial side.

Figure 5B:
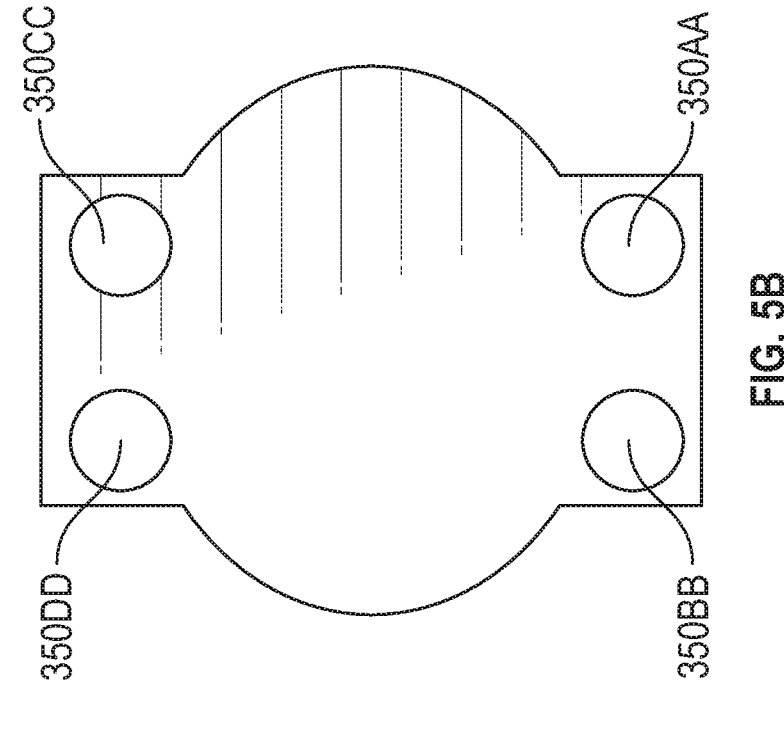
FIG. 5B is a bottom view of another embodiment of an array of sensors of an example sensor assembly that can be used with the ground contact sensor array of FIGS. 1-4.

The array 500 of the sensors 350 may include seven sensors 350 as illustrated in FIG. 5. In some aspects, the array 500 may include less than or more than seven sensors 350. The array 500 may include four sensors 350 as shown in FIG. 5B. The array 500 may include ten, fifteen, twenty, thirty, or more sensors. The sensors 350 may be positioned such that one or more line symmetry and/or point symmetry may exist. The sensors 350 may define the sagittal plane and/or coronal plane.

In some embodiments, as discussed above, the sensor assembly 300 can includes one or more magnets 340. The number of magnets 340 and the sensors 350 used for detecting different load conditions may be the same or different. As shown in FIGS. 4 and 5, the sensor assembly 300 may include four magnets 340 and seven sensors 350. Different combinations of numbers of magnets 340 and sensors 350 may be used to capture the relative motions of the base 200 of the distal connector 108 and the frame 302 of the sensor assembly 300. In some embodiments, the magnets 340 may be coupled to a non-moving body of the POD while the sensors 350 may be coupled to a moving body of the POD.

The locations of the sensors 350 on the PCB 400 may represent different locations of the sensor assembly 300 or a load-bearing area of the prosthetic device 100. For example, the load-bearing surface may be a bottom of a prosthetic or orthotic foot or an ankle. With respect to FIG. 5A, the sensors 350A and 350B, for example, may represent the posterior portion/area of a prosthetic or orthotic foot, while the sensors 350F and 350G may represent the anterior portion/area of the prosthetic or orthotic foot. More specifically, the sensors 350A and 350B may represent the heel of the prosthetic or orthotic foot, while the sensors 350F and 350G may represent the toes of the prosthetic or orthotic foot. The sensors 350C-350E may represent the mid-section of the prosthetic or orthotic foot. Likewise, the sensors 350B, 350E, and 350G may represent medial (or lateral) side of a prosthetic or orthotic foot, while the sensors 350A, 350C, and 350F may represent lateral (or medial) side. In this regard, for example, the sensor 350G, may represent a medial-anterior region of a load-bearing surface of a prosthetic foot.

FIGS. 6A-6D illustrate data 650A-650G collected by the sensors 350A-350G of the array 500, respectively, during a stance phase of a gait cycle on a level surface by a right side amputee. In this example, the sensors 350A and 350B may represent the posterior area of a load-bearing surface of the prosthetic device 100, the sensors 350F and 350G the anterior portion, the sensors 350B, 350E, and 350G medial portion, and the sensors 350A, 350C, and 350F lateral portion. It may be observed that sensors located on the same row (for example, sensors 350A and 350B, or sensors 350F and 350G) do not present the same response at the same point in time during the stance phase. FIGS. 6A-6D illustrates data collected by each row (that is, rear (posterior), middle, and front (anterior) rows as shown in FIG. 5A). FIGS. 6A-6D show progression of a load line through sensor rows and coronal plane alignment. With respect to FIGS. 6A-6D, data points 650A-650G may represent the signal collected by the sensors 350A-350G shown in FIG. 5A.

At initial contact, it may be observed that a posterior-medial sensor (that is, the sensor 350B) experiences a load that is greater than a load experienced by a rear-lateral sensor (e.g., the sensor 350A). In addition, it may be observed that the sensor 350B experiences higher load than the sensor 350A during the entire stance phase. FIGS. 6C and 6D illustrate that middle and anterior row sensors also register load at the initial contact of the heel. This observation may arise from the array 500 of the sensor 350 and the position of the load. Since the hip is flexed at foot strike, the load line is in front of a posterior portion of the base 200, and may cause displacement of the anterior sensors as well. As the roll over the foot progresses, the load line may move towards toes, which may result in reduced displacement of the posterior and middle sensors, as illustrated in FIG. 6C. Since the load line is at the front of the base 120, posterior components of the sensor assembly 300 are undergoing a distal pull, which reduces the signal strength from posterior and middle row sensors (that is, 350A, 350B, 350C, 350D, and 350E). As the roll over progresses, medial-anterior loading amplitude (that is, signal from the sensor 350G) increases as late stance rotation on the big toe occurs.

Figure 6A:
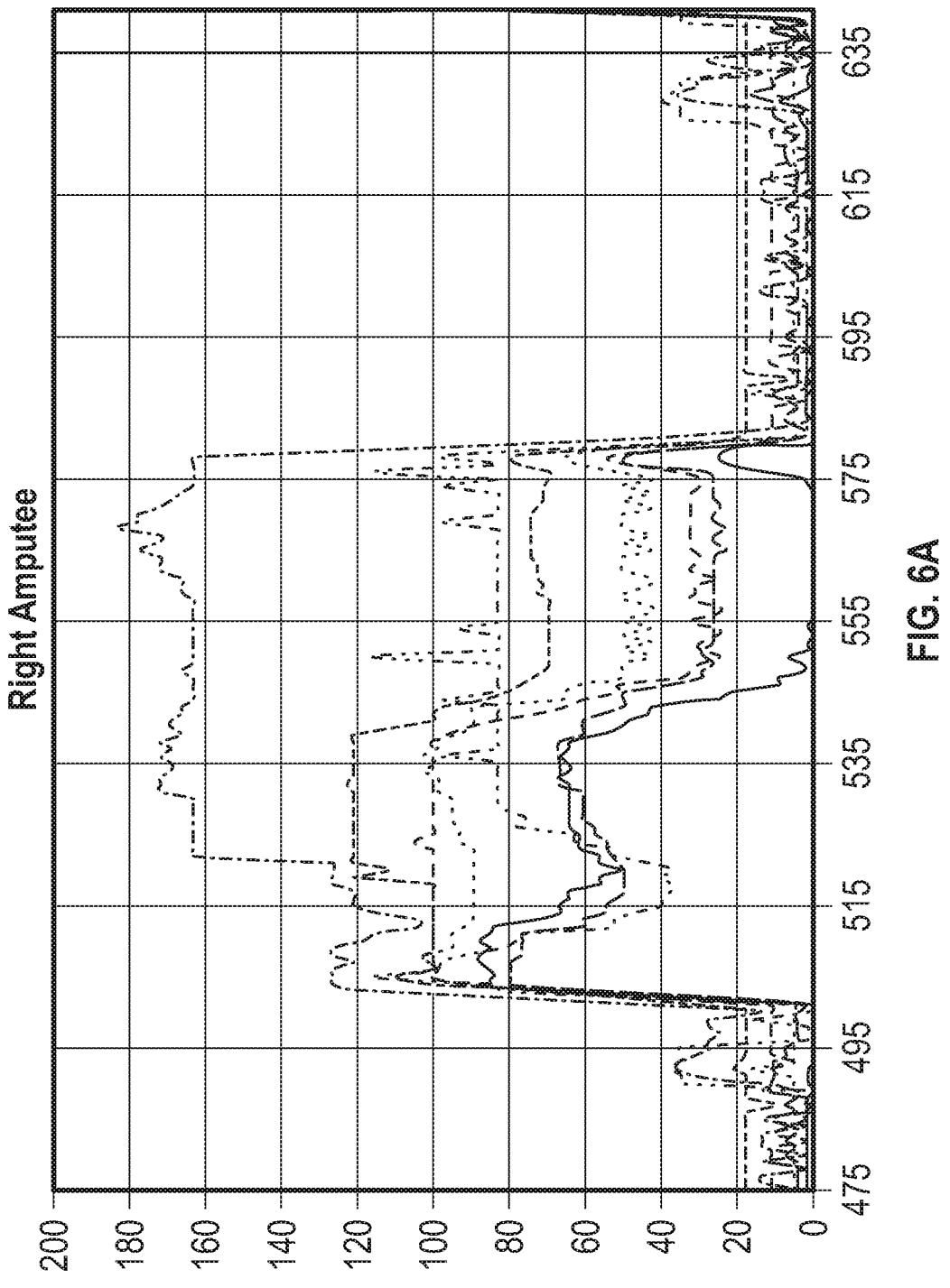
FIGS. 6A-6D are data plots showing example load pattern data produced from an embodiment of an array of ground contact sensors during a swing and a stance phase of a gait cycle.
Figure 6B:
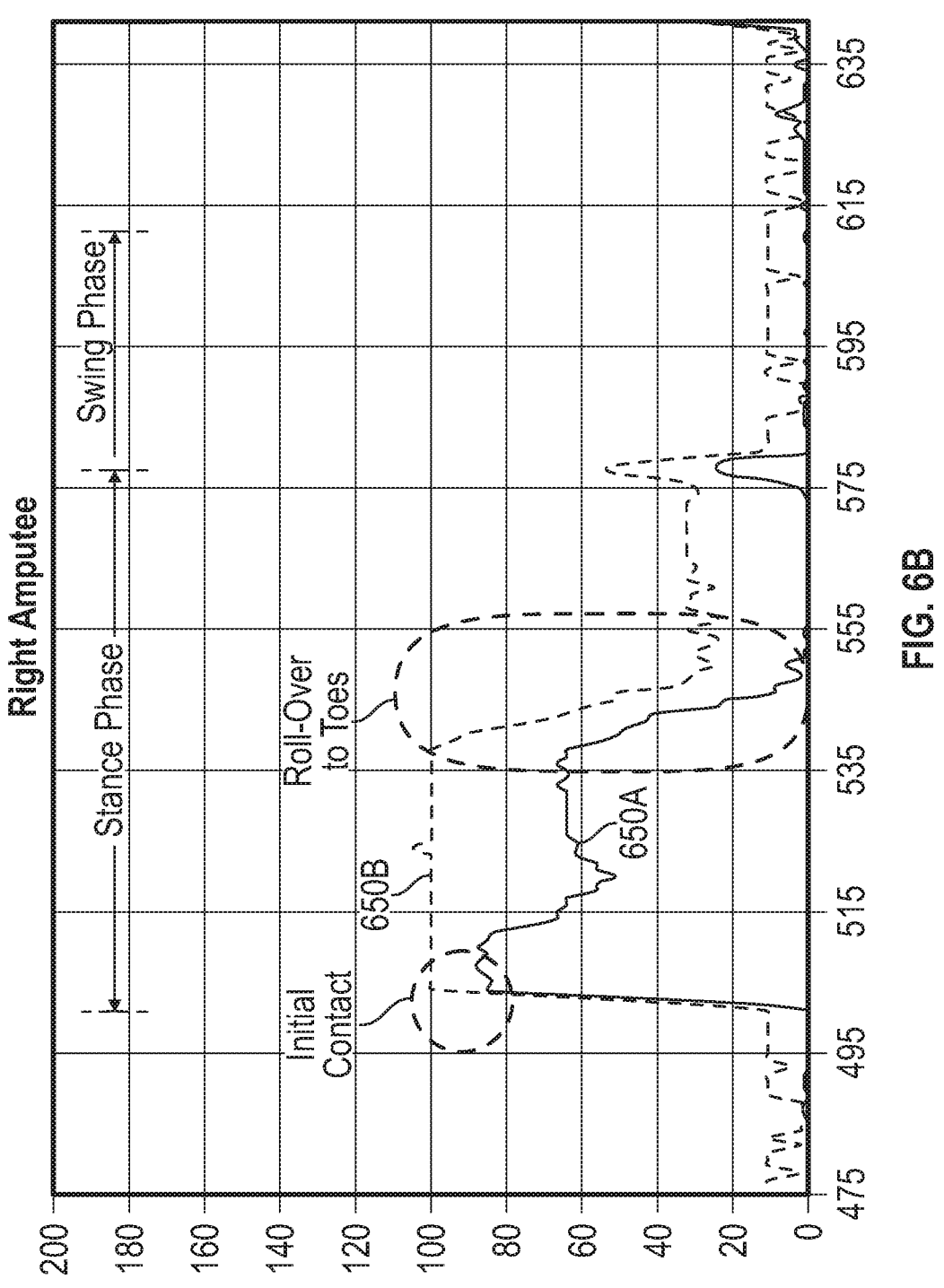
Figure 6C:
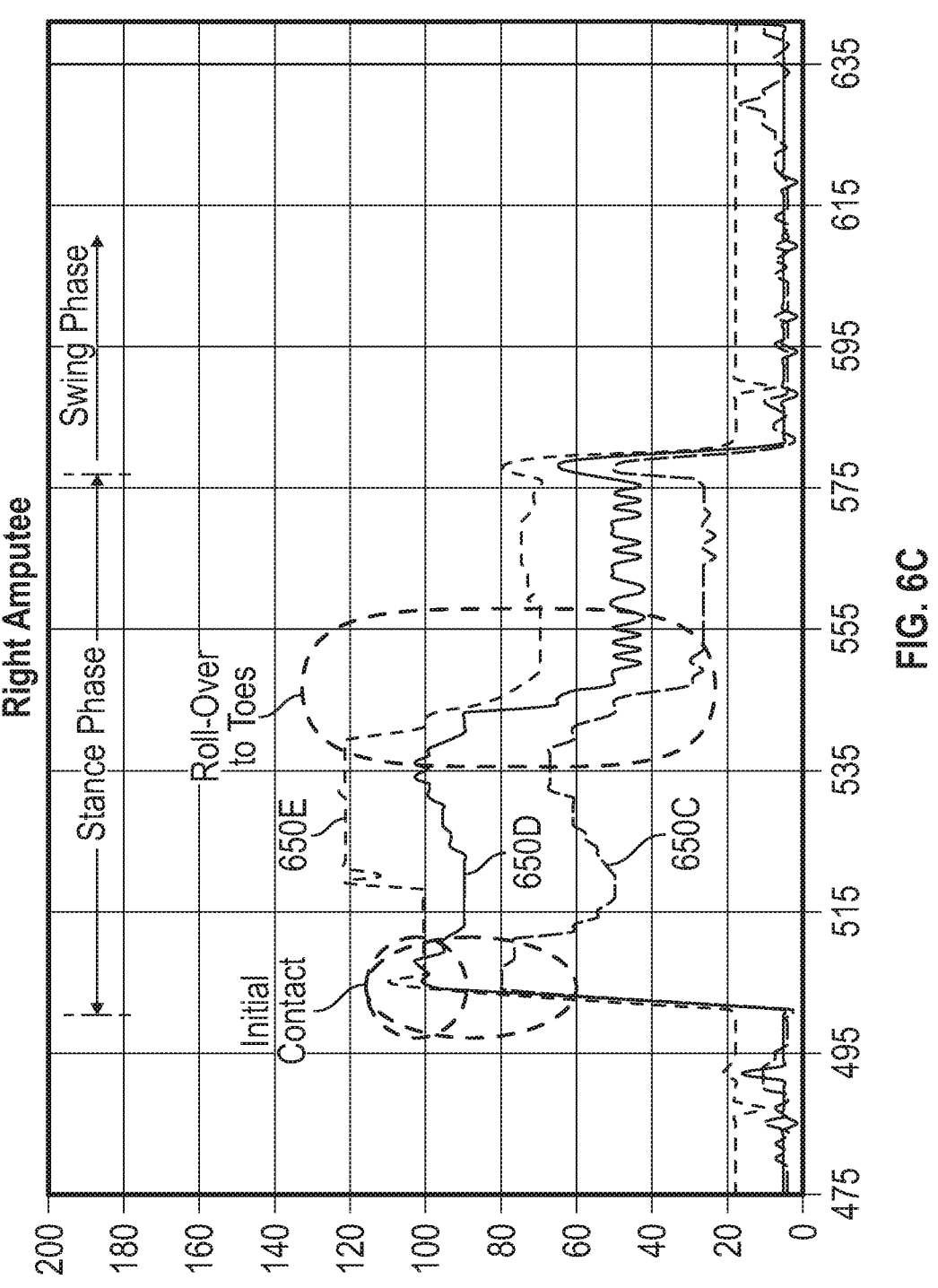
Figure 6D:
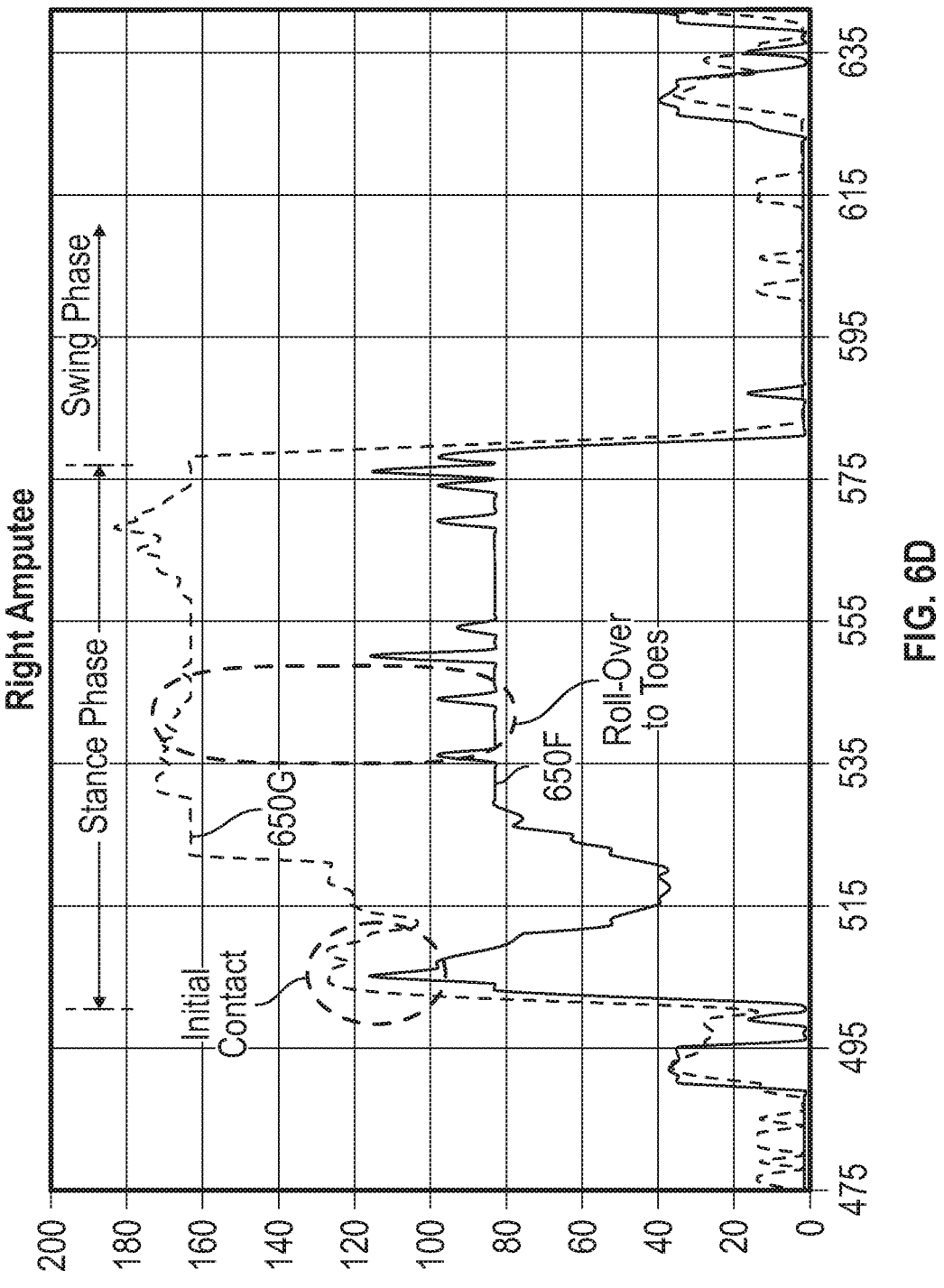

Using the sensor array 500, it is then possible to follow the load line progression (that is, the amplitude of the signals received from the sensors 350A-350G) in the coronal and/or sagittal plane while avoiding area of low sensitivity, as seen on the lateral sensors of the posterior and middle rows in FIGS. 6B and 6C.

The data and the results shown in FIGS. 6A-6D and discussed above do not limit the subject matter disclosed herein any way. For example, depending on the user of the prosthetic device 100, it is possible that there may be a lateral side loading bias during a stance phase of a gait cycle. In some other examples, load may transfer from the posterior-medial portion to the anterior-lateral portion, or from the posterior-lateral portion to the anterior-medial portion. Different types of load patterns during a stance phase of a gait cycle may be analyzed and those load patterns may be used to detect ground contacts. Using an array to capture and analyze load patterns may be advantageous in recognizing different and/or abnormal gait characteristics and/or types for different users of prosthetic devices, and those load patterns may be used to provide specific actuator outputs to assist users with normal, different, or abnormal gait characteristics.

Similar results may be obtained using an array 500A shown in FIG. 5B, where sensors 350 (sensor 350AA, sensor 350BB, sensor 350CC, and sensor 350DD) are located in the corners. In this example, the sensors 350AA and 350BB may be located on the posterior portion of the sensor assembly 300 and may represent load applied to the posterior portion of a load-bearing surface/area of the prosthetic device 100. Likewise, the sensors 350CC and 350DD may be located on the anterior portion of the sensor assembly 300 and may represent load applied to the anterior portion of the load-bearing surface/area.

Figure 7A:
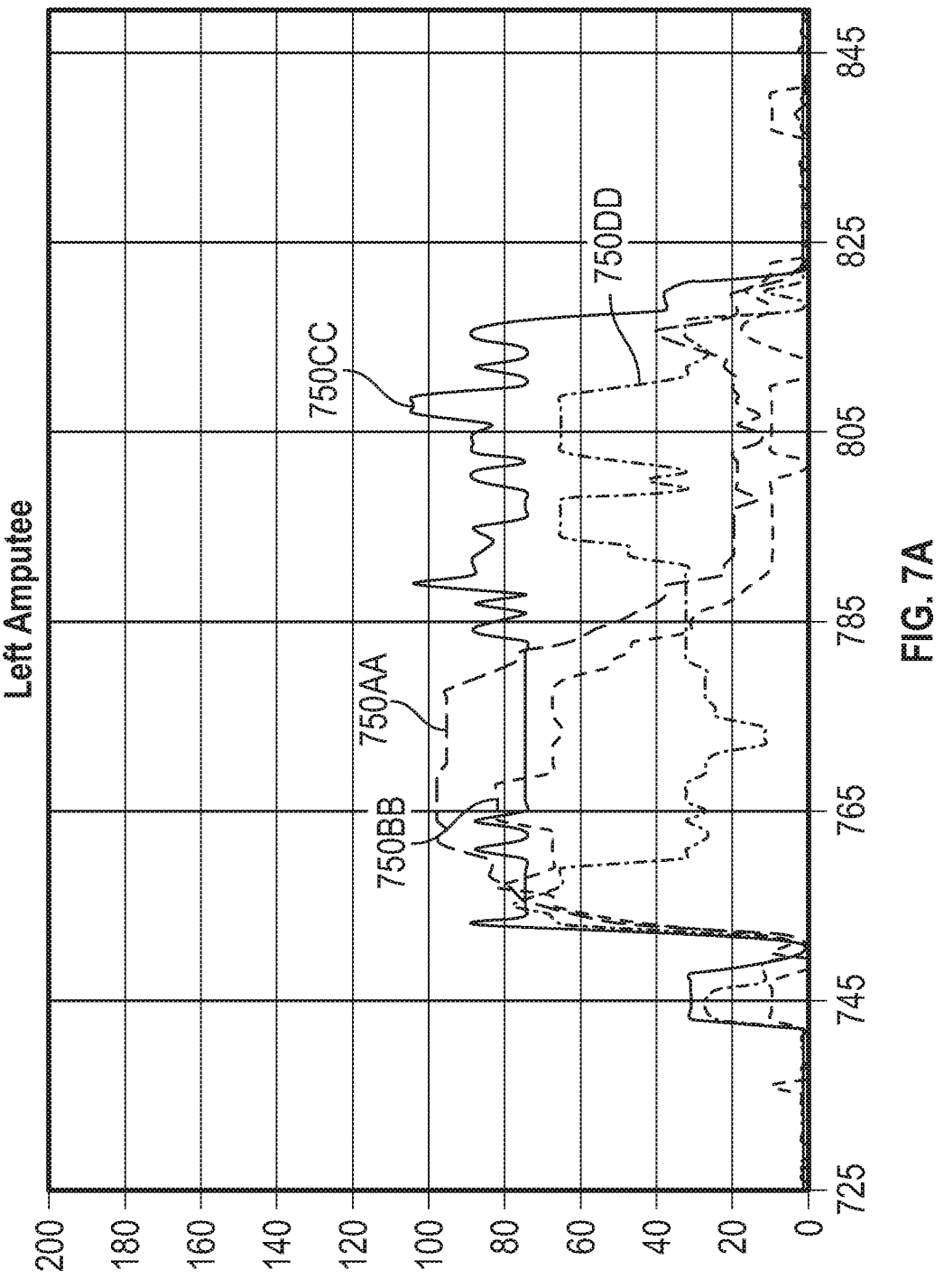
FIGS. 7A-7B are data plots showing further example load pattern data produced from an embodiment of an array of ground contact sensors during a swing and a stance phase of a gait cycle.
Figure 7B:
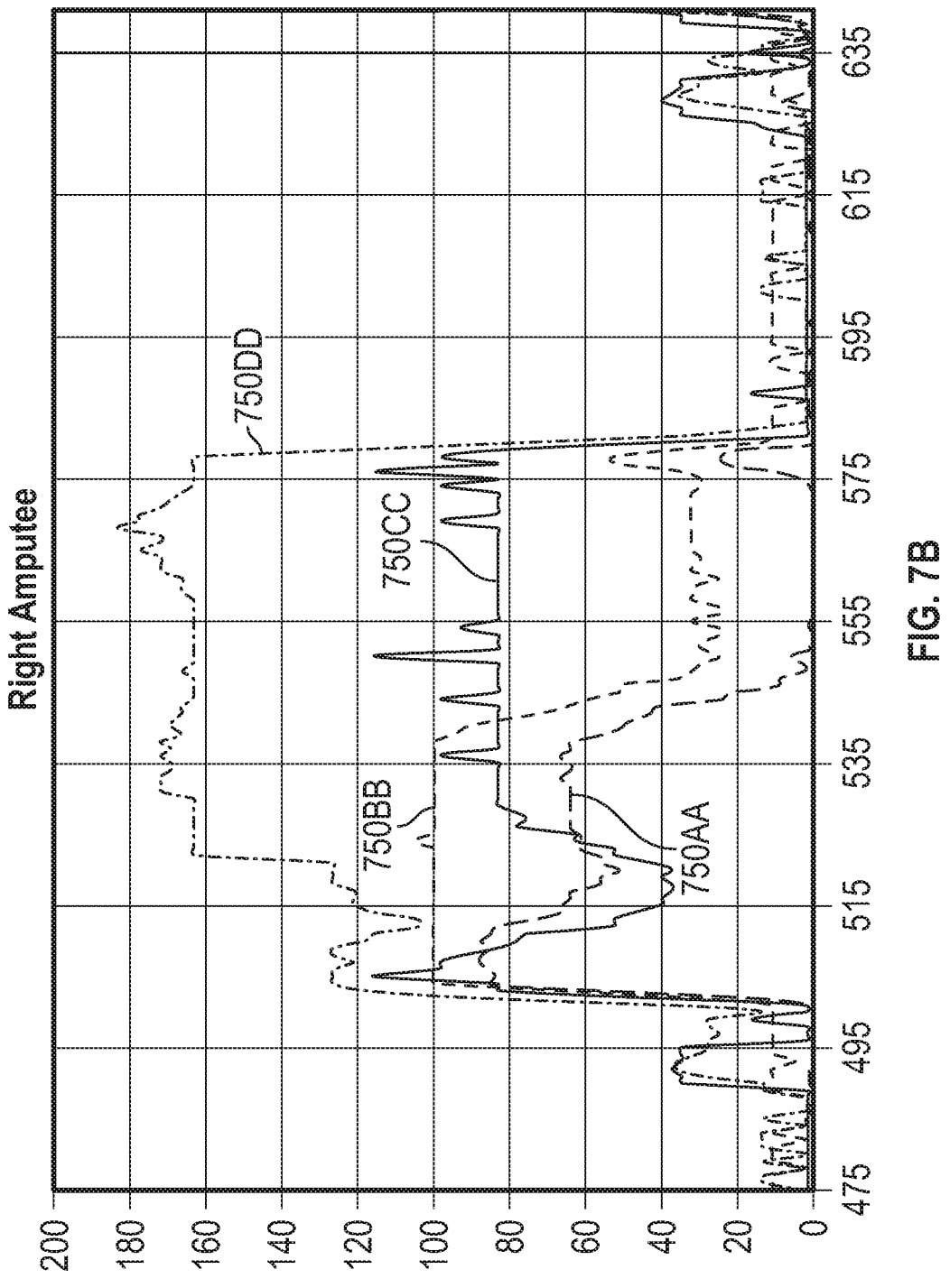

FIGS. 7A and 7B illustrate graphical illustration of data 750AA-750DD collected by the sensors 350AA-350DD as shown in FIG. 5B. Results from two different amputees using the same prosthetic device are compared, where FIG. 7A illustrates data collected from a left-side amputee, while FIG. 7B illustrates data collected from a right-side amputee. It may be observed from these plots that the dominant signal source between the two plots is inverted. For the left amputee, the sensor 350AA experienced load greater than the sensor 350BB, while for the right amputee, the sensor 350BB experienced load greater than the sensor 350AA. This indicates that the loading was biased towards the medial side of the heel, as per expected from gait biomechanics. In other words, the relative displacement between the sensor assembly 300 and the base 200 was greater in the medial side than in the lateral side. In both cases, the array 500A was able to properly record a load cycle, regardless of whether a user was an left amputee or a right amputee. Similar characteristic may be observed for the anterior sensors (that is, the sensors 350CC and 350DD) in the later portions of the stance phase of a gait cycle. Readings from the sensors 350CC and 350DD may be inverted in amplitude between the two amputees as the medial side sensor shows higher loading than the lateral sensor. For the left amputee, the sensor 750CC (that is, anterior-medial sensor) experienced load greater than load experienced by the sensor 750DD (that is, anterior-lateral sensor). Likewise, for the right amputee, the sensor 750DD (that is, anterior-medial sensor) experienced load greater than load experienced by the sensor 750CC (that is, anterior-lateral sensor).

It is to be noted that the difference in amplitude may be attributed to a difference in body weight between users or different gait characteristics or abnormalities.

Use of a sensor array pattern in-line with the nature of the loads and typical loading patterns observed during gait allows the sensors 350 to sense load applied during a stance phase of a gait cycle. In addition, using different sensor array patterns may allow the prosthetic device 100 to identify different foot-ground interactions, as discussed above. It is also possible to further strengthen the robustness of the ground contact sensor function by adding signal processing, either in hardware or in firmware. Since there is no a priori knowledge of the amputation side or the characteristic progression of the load line during ambulatory or non-ambulatory gait activities, there is a benefits in processing the raw signals, similar to the one shown in the figures above, such that prosthetic device performance is maintained in all use-cases.

One aspect of a software process merging the information provided by the individual sensors (for example, the sensors 350A-350G) present in an array may include creating a contour plot from the individual sensor signals. In the context of a control system managing actuator behavior/operation by utilizing information regarding the interaction of a prosthetic device with the ground surface, a contour plot allows to sum contribution of all sensors. The contour plot may be generated by adding all the partial loading observed through the measurement points by all sensors. A contour plot of the data collected by an array of sensors may then present the total observed loading, which indicate a presence, or a lack of presence, of an interaction between the prosthetic foot and the ground. A simple hysteretic threshold process may then be used to determine whether the interaction is present or not. Additionally and/or alternatively, the contour plot may a pattern of the load applied to the prosthetic limb.

A simple contour plot may be created for a sensor assembly 300 implementing four sensors 350AA-350DD, such as shown in FIGS. 7A and 7B, in real-time through a relation of the form:

$$A_t = S_{1,t} + S_{2,t} + S_{4,t}$$

where $A_t$ is the contour Amplitude at time t and $S_{x,t}$ is sensor x signal amplitude at time t.

Figure 8A:
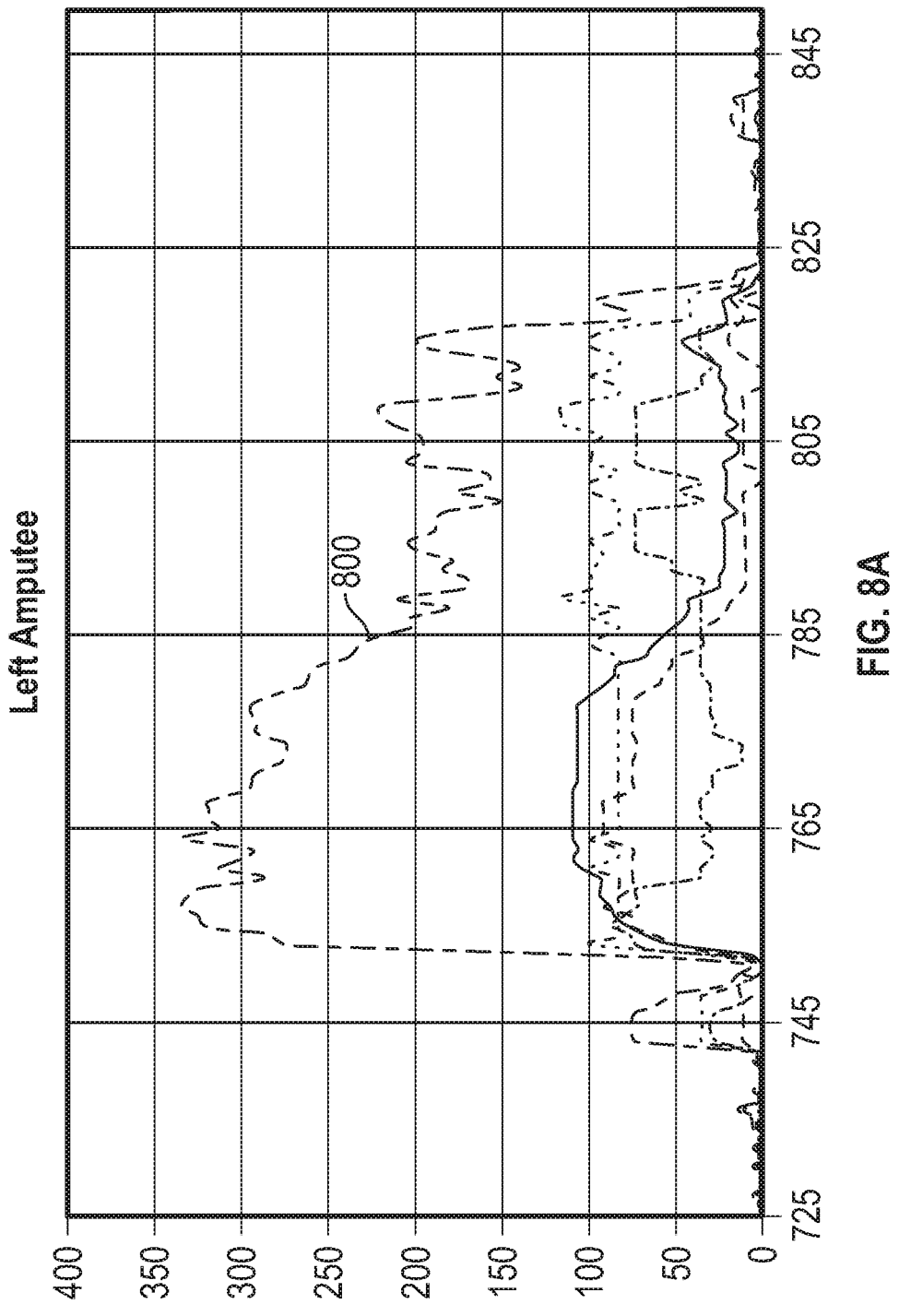
FIGS. 8A-8B are data plots showing an example contour plot resulting from analysis of the load data of FIGS. 7A-7B.

FIG. 8A shows an example contour plot 800 generated by using the data illustrated in FIG. 7A. Such process may increase the signal amplitude and preserve the general shape attributes over the stance phase load cycle. Use of contour plot processing may minimize impacts of signals characteristics that are not coherent across all sensors in the array, and in facts may be used as a weak majority voting scheme at the same time. Characteristics that are common across all signals will get amplified.

Another hardware or firmware based signal processing scheme that may be used to combine the information provided by multiple sensors present in an array is using a maximum filtering scheme. In the maximum filtering scheme, the sensor signal presenting the highest amplitude is considered as the only valid one. Such processing scheme may take the following form when implemented as a real-time process:

$$A_t = \max(S_{1,t}, S_{2,t}, S_{3,t}, S_{4,t})$$

where $A_t$ is the maximum amplitude at time t and $S_{x,t}$ is sensor x signal amplitude at time t.

Figure 8B:
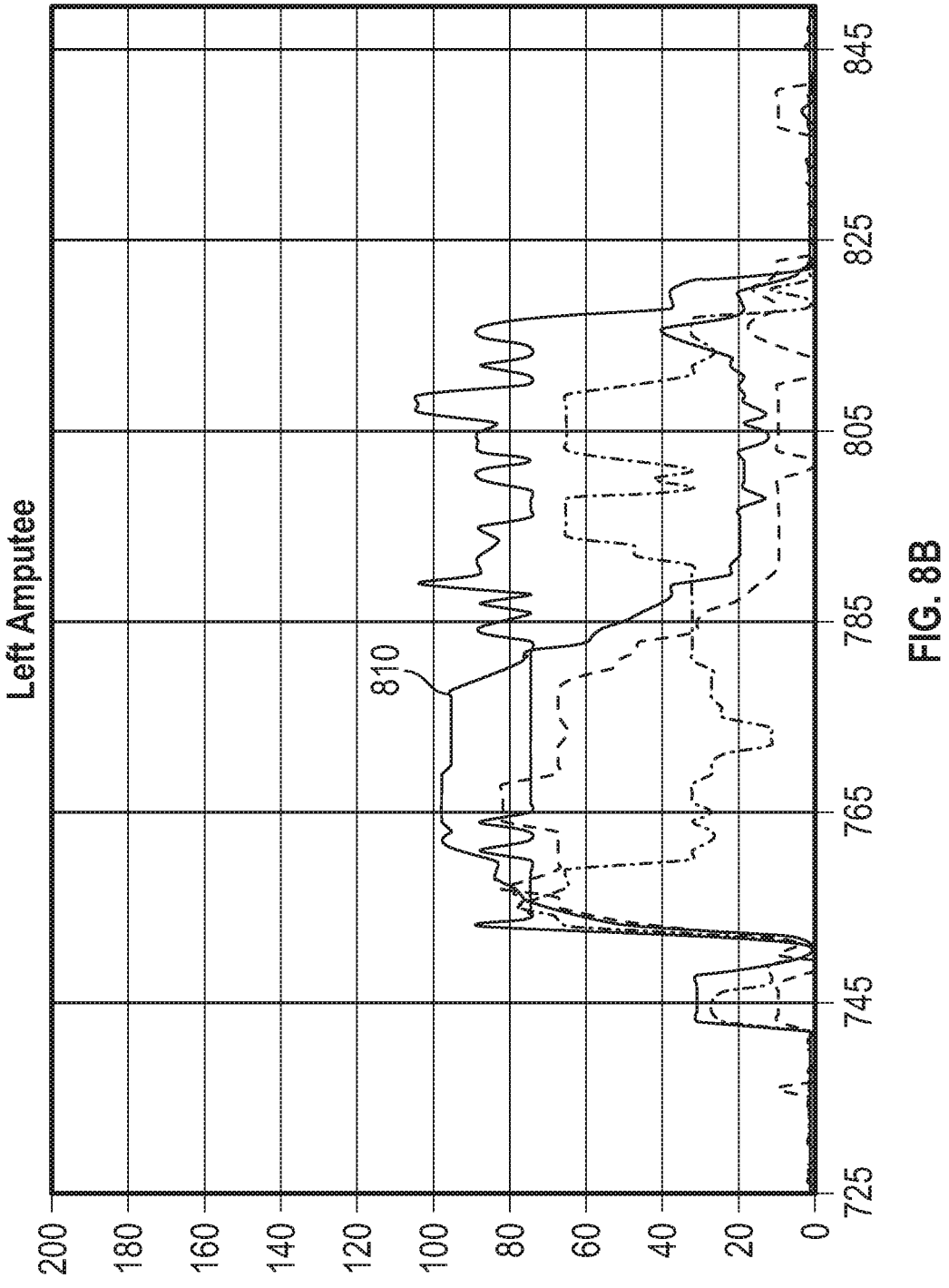

FIG. 8B illustrates an example plot 810 after applying the above maximum filter to the data presented in FIG. 7A above. With reference to FIG. 7A, it may be observed that the plot 810 follows readings from the sensor 350AA (that is, a posterior-medial sensor) until mid-stance (after a few rapid transition during a heel strike) before switching to readings from the sensor 350CC (that is, an anterior-medial sensor) at the start of a rollover to the toes until loading is removed.

Additional and/or alternatively, other signal processing approaches may be used for firmware processing of the data streams, such as heuristic rule-based decisions or weighted average.

Additionally and/or alternatively, dependencies on the load line progression pattern could be extracted and use for either prosthetic device control, gait quality assessment or providing guidance on prosthetic foot alignment. For example, load line progression pattern may be analyze to detect different gait characteristics including, but not limited to, walking speed, cadence, stance time, swing time, double support time, step length, step width, walking angle, toe angle, and the like. In some aspects, different types of gait abnormalities including, but not limited to, hemiplegic gait, diplegic gait, neuropathic gait, myopathic gait, choreiform gait, ataxic gait, Parkinsonian gait, sensory gait, and the like by analyzing load line progression pattern.

Additionally and/or alternatively, load line progression pattern of a specific user may be collected using the sensor assembly described above and be used to generate a user-specific methodology and/or signal processing algorithms/approaches. Such methodologies and/or signal processing algorithms/approaches may be used to detect different phases (for example, a stance phase and a swing phase) of the user's gait cycle. In this regard, prosthetic devices may utilize a ground contact sensor assembly described above to accurately detect ground contacts for any user's gait cycle and, in turn, provide signals to operate its actuator to provide adequate stance phase control.

The graphical illustrates shown in figures above are for illustrative purposes only and does not limit the subject matter disclosed herein in any way.

Various example embodiments of apparatuses, methods, and systems relating to a ground-contact sensor array for a prosthetic device can be found in the following clauses:

Clause 1. A ground-contact sensor array for a lower limb prosthetic device, the ground-contact sensor array comprising:

a first body configured to attach to a distal portion of a shank of the lower limb prosthetic device and having a first portion configured to remain stationary relative to the shank, the first body comprising a second portion configured to compress in response to a ground contact load applied to the lower limb prosthetic device;

a second body moveably attached to and located distally of the first body and comprising a distal connector configured to attach to a prosthetic foot or ankle, the second body configured to translate and/or rotate relative to the first body in response to the ground contact load applied to the lower limb prosthetic device to cause the second portion of the first body to compress; and a plurality of sensors coupled with a proximal portion of the first body and configured to generate data related to a plurality of distances from the plurality of sensors to respective target portions of the second body in response to translation and/or rotation of the second body relative to the first body, wherein the data is indicative of location of the second body relative to the first body, which is indicative of ground contact by the lower limb prosthetic device.

Clause 2. The ground-contact sensor array of Clause 1, wherein the plurality of sensors comprises Hall effect sensors and the respective target portions of the second body comprise magnets.

Clause 3. A ground-contact sensor array for a lower limb prosthetic device, the ground-contact sensor array comprising:

a first body configured to attach to a shank of the lower limb prosthetic device;

a second body moveably attached to the first body and comprising a distal connector configured to attach to a prosthetic foot or ankle; and a plurality of sensors coupled with the first or second body and configured to generate data related to a plurality of distances between the first and second body. Clause 4. The ground-contact sensor array of Clause 3, wherein the plurality of sensors are coupled with the first body.

Clause 5. The ground-contact sensor array of Clause 3, wherein the plurality of sensors comprise non-contact distance sensors coupled with the first or second body and configured to generate data related to a plurality of distances to respective portions of the other of the first or second body.

Clause 6. The ground-contact sensor array of any of Clauses 3 or 5, further comprising a plurality of magnets coupled with the first or second body, wherein the plurality of sensors comprises a plurality of Hall effect sensors coupled with the other of the first or second body, and wherein each Hall effect sensor is configured to generate data related to a respective distance to a respective magnet.

Clause 7. The ground-contact sensor array of any of Clauses 3 to 6, wherein the data related to a plurality of distances comprises first data related to a plurality of first distances and second data related to a plurality of second distances, wherein the first or second data are generated in response to a non-inertial load applied to the lower limb prosthetic device, and wherein the first and second data are indicative of at least one of the plurality of first distances being different than at least one of the plurality of second distances.

Clause 8. The ground-contact sensor array of any of Clauses 3 to 7, wherein the plurality of sensors are arranged in a transverse plane.

Clause 9. The ground-contact sensor array of any of Clauses 3 to 8, wherein the first body is configured to not move relative to the shank and the second body is configured to move relative to the first body.

Clause 10. The ground-contact sensor array of any of Clauses 3 to 9, wherein the first body comprises a selectively compliant structure, the selectively compliant structure comprising:

a first pair of beams located on a medial side of the first body and extending in an anterior-posterior direction, each beam of the first pair of beams spaced axially apart from each other; and a second pair of beams located on a lateral side of the first body and extending in the anterior-posterior direction, each beam of the second pair of beams spaced axially apart from each other.

Clause 11. The ground-contact sensor array of Clause 10, further comprising a first bridge axially connecting the first pair of beams and a second bridge axially connecting the second pair of beams.

Clause 12. The ground-contact sensor array of any of Clauses 3 to 11, wherein the data related to a plurality of distances between the first and second body is generated in response to a ground-contact load applied to the first or second body during a stance phase of a gait cycle.

Clause 13. The ground-contact sensor array of any of Clauses 3 to 12, wherein the plurality of sensors are configured to generate data related to a predetermined plurality of axial distances between the first and second body when no load is exerted on the second body.

Clause 14. The ground-contact sensor array of any of Clauses 3 to 13, wherein the first body and second body define a plurality of gaps therebetween.

Clause 15. The ground-contact sensor array of Clause 14, wherein the plurality of gaps are located between anterior and posterior ends of the first and second bodies.

Clause 16. The ground-contact sensor array of Clause 14, wherein the gaps change in size in response to changes in relative movement between the first and second body.

Clause 17. The ground-contact sensor array of Clause 14, wherein the first body is attached to a raised surface of the second body located between the plurality of gaps.

Clause 18. A ground-contact sensor array for a lower limb prosthetic device, the ground-contact sensor array comprising:

a first body configured to attach to a first portion of a lower limb prosthetic device that is located proximally of the first body;

a second body moveably attached to the first body and configured to attach to a second portion of the lower limb prosthetic device that is located distally of the second body; and a plurality of sensors attached to the first or second body, wherein each sensor is configured to detect a respective distance between the sensor and a respective target of the other of the first or second body.

Clause 19. The ground-contact sensor array of Clause 18, wherein the plurality of sensors are attached to the first body and each sensor is configured to detect a respective distance between the sensor and the respective target of the second body.

Clause 20. The ground-contact sensor array of any of Clauses 18 to 19, wherein the respective target comprises a respective portion of the other of the first or second body.

Clause 21. The ground-contact sensor array of any of Clauses 18 to 20, wherein the plurality of sensors comprises a plurality of Hall effect sensors and the respective target comprises a respective magnet.

Clause 22. The ground-contact sensor array of any of Clauses 18 to 21, wherein the plurality of sensors are configured to generate a first set of data based at least on location of the first body relative to the second body, wherein the plurality of sensors are positioned in an array such that the first set of data represent distances at different locations to the other of the first or second body, and wherein the first set of data is representative of amount of load applied to different locations of the moving body and thereby provide a load pattern across the second body.

Clause 23. A lower limb prosthetic device comprising the ground-contact sensor array of any of Clauses 1-22.

Clause 24. A method of detecting ground-contact by a lower limb prosthetic device, the method comprising:

detecting first data related to a plurality of first distances between each sensor of a plurality of sensors and a moving body of the lower limb prosthetic device;

detecting second data related to a plurality of second distances between each sensor of the plurality of sensors and the moving body of the lower limb prosthetic device; and determining that the lower limb prosthetic device has contacted ground based on the first and second data.

Clause 25. The method of Clause 24, further comprising:

detecting, using each of the plurality of sensors, a magnetic field generated by a plurality of magnets;

determining a magnitude of the magnetic field detected by each of the plurality of sensors; and calculating the plurality of second distances based at least on the magnitude of the magnetic field.

Clause 26. A non-transitory computer readable medium having stored thereon a set of instructions that when executed by a processor performs a method of detecting ground-contact by a lower limb prosthetic device, the method comprising method of detecting ground-contact by a lower limb prosthetic device, the method comprising:

detecting first data related to a plurality of first distances between each sensor of a plurality of sensors and a moving body of the lower limb prosthetic device;

detecting second data related to a plurality of second distances between each sensor of the plurality of sensors and the moving body of the lower limb prosthetic device; and determining that the lower limb prosthetic device has contacted ground based on the first and second data.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment may be used with a different embodiment described herein and the combination still fall within the scope of the disclosure. It should be understood that various features and aspects of the disclosed embodiments may be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations, one or more features from a claimed combination may, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described may be incorporated in the example methods and processes. For example, one or more additional operations may be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems may generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "may," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially"

as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A ground-contact sensor array for a lower limb prosthetic device, the ground-contact sensor array comprising:
    a first body configured to attach to a distal portion of a shank of the lower limb prosthetic device and having a first portion configured to remain stationary relative to the shank, the first body comprising a second portion configured to compress in response to a ground contact load applied to the lower limb prosthetic device;
    a second body moveably attached to and located distally of the first body and comprising:
        a distal connector configured to attach to a prosthetic foot or ankle, and
        a raised portion on a surface of the second body proximate to the first body, wherein the second body is configured to rotate about the raised portion and to translate relative to the first body in response to the ground contact load applied to the lower limb prosthetic device to cause the second portion of the first body to compress;
    a plurality of sensors coupled with a proximal portion of the first body; and
    a plurality of target portions coupled to the second body, wherein each one of the plurality of sensors corresponds to a respective target portion of the plurality of target portions, and wherein the plurality of sensors are configured to generate data based on one or more changes in a plurality of distances from the plurality of sensors to respective target portions of the plurality of target portions coupled to the second body in response to translation and/or rotation of the second body relative to the first body, wherein the data is indicative of location of the second body relative to the first body, which is indicative of ground contact by the lower limb prosthetic device.

2. The ground-contact sensor array of claim 1, wherein the plurality of sensors comprises Hall effect sensors and the respective target portions of the second body comprise magnets.

3. A ground-contact sensor array for a lower limb prosthetic device, the ground-contact sensor array comprising:
    a first body configured to attach to a shank of the lower limb prosthetic device;
    a second body moveably attached to the first body and comprising a distal connector configured to attach to a prosthetic foot or ankle, a surface of the second body proximate to the first body comprising a raised portion, wherein the second body is configured to rotate about the raised portion and to translate relative to the first body in response to a ground contact load applied to the lower limb prosthetic device; and
    a plurality of sensors coupled with the first or second body and configured to generate data based on one or more changes in a plurality of distances between the first and second body.

4. The ground-contact sensor array of claim 3, wherein the plurality of sensors are coupled with the first body.

5. The ground-contact sensor array of claim 3, wherein the plurality of sensors comprise non-contact distance sensors coupled with the first or second body and configured to generate data based on one or more changes in a plurality of distances to respective portions of the other of the first or second body.

6. The ground-contact sensor array of claim 3, further comprising a plurality of magnets coupled with the first or second body, wherein the plurality of sensors comprises a plurality of Hall effect sensors coupled with the other of the first or second body, and wherein each Hall effect sensor is configured to generate data based on a change in a respective distance to a respective magnet.

7. The ground-contact sensor array of claim 3, wherein the data based on one or more changes in a plurality of distances comprises first data based on one more changes in a plurality of first distances and second data based on one or more changes in a plurality of second distances, wherein the first or second data are generated in response to a non-inertial load applied to the lower limb prosthetic device, and wherein the first and second data are indicative of at least one of the plurality of first distances being different than at least one of the plurality of second distances.

8. The ground-contact sensor array of claim 3, wherein the plurality of sensors are arranged in a transverse plane.

9. The ground-contact sensor array of claim 3, wherein the first body is configured to not move relative to the shank and the second body is configured to move relative to the first body.

10. The ground-contact sensor array of claim 3, wherein the first body comprises a selectively compliant structure, the selectively compliant structure comprising:
    a first pair of beams located on a medial side of the first body and extending in an anterior-posterior direction, each beam of the first pair of beams spaced axially apart from each other; and
    a second pair of beams located on a lateral side of the first body and extending in the anterior-posterior direction, each beam of the second pair of beams spaced axially apart from each other.

11. The ground-contact sensor array of claim 10, further comprising a first bridge axially connecting the first pair of beams and a second bridge axially connecting the second pair of beams.

12. The ground-contact sensor array of claim 3, wherein the data based on one or more changes in the plurality of distances between the first and second body is generated in response to a ground-contact load applied to the first or second body during a stance phase of a gait cycle.

13. The ground-contact sensor array of claim 3, wherein the plurality of sensors are configured to generate data based on one or more changes in a predetermined plurality of axial distances between the first and second body when no load is exerted on the second body.

14. The ground-contact sensor array of claim 3, wherein the first body and the raised portion of the second body define a plurality of gaps between the first body and the second body, and wherein the gaps change in size in response to changes in relative movement between the first and the second body.

15. The ground-contact sensor array of claim 14, wherein the first body is attached to the raised portion of the second body located between the plurality of gaps.

16. A ground-contact sensor array for a lower limb prosthetic device, the ground-contact sensor array comprising:

a first body configured to attach to a first portion of a lower limb prosthetic device that is located proximally of the first body;

a second body moveably attached to the first body and configured to attach to a second portion of the lower limb prosthetic device that is located distally of the second body, a surface of the second body proximate to the first body comprising a raised portion, wherein the second body is configured to rotate about the raised portion and to translate relative to the first body in response to a ground contact load applied to the lower limb prosthetic device; and a plurality of sensors attached to the first or second body, wherein each sensor is configured to detect a respective distance between the sensor and a respective target of the other of the first or second body.

17. The ground-contact sensor array of claim 16, wherein the plurality of sensors are attached to the first body and each sensor is configured to detect a respective distance between the sensor and the respective target of the second body.

18. The ground-contact sensor array of claim 16, wherein the respective target comprises a respective portion of the other of the first or second body.

19. The ground-contact sensor array of claim 16, wherein the plurality of sensors comprises a plurality of Hall effect sensors and the respective target comprises a respective magnet.

20. The ground-contact sensor array of claim 16, wherein the plurality of sensors are configured to generate a first set of data based at least on location of the first body relative to the second body, wherein the plurality of sensors are positioned in an array such that the first set of data represent distances at different locations to the other of the first or second body, and wherein the first set of data is representative of amount of load applied to different locations of the second body and thereby provide a load pattern across the second body.

* * * * *